(12) United States Patent
Pignot et al.

(10) Patent No.: US 6,875,750 B1
(45) Date of Patent: Apr. 5, 2005

(54) AZIRIDINE COMPOUNDS AND METHODS OF MAKING AND USING THEM

(75) Inventors: Marc Pignot, Bad Soden (DE); Elmar Weinhold, Aachen (DE)

(73) Assignee: Max-Planck-Gesellschaft zur Foerderung der Wissenschaften E.V., Berlin (DE)

( * ) Notice: Subject to any disclaimer, the term of this patent is extended or adjusted under 35 U.S.C. 154(b) by 0 days.

(21) Appl. No.: 09/744,641

(22) PCT Filed: Jul. 28, 1999

(86) PCT No.: PCT/EP99/05405

§ 371 (c)(1),
(2), (4) Date: Jul. 27, 2001

(87) PCT Pub. No.: WO00/06587

PCT Pub. Date: Feb. 10, 2000

(30) Foreign Application Priority Data

Jul. 29, 1998 (EP) .............................................. 98114201

(51) Int. Cl.[7] .................. A01N 43/04; A61K 31/70
(52) U.S. Cl. .................. 514/45; 514/46; 536/25.34; 536/25.3; 536/23.1; 536/22.1; 536/25.31; 536/26.1; 536/26.32; 536/26.13; 435/6; 435/7.1; 435/7.4; 435/7.771; 435/7.72; 534/558; 534/560; 534/639
(58) Field of Search .................. 536/25.34, 25.3, 536/23.1, 22.1, 25.31, 26.1, 26.32, 26.13, 26.12; 514/45, 46; 435/6, 7.1, 7.4, 7.71, 7.72; 534/558, 560, 639

(56) References Cited

PUBLICATIONS

Djordjevic and Stock, "Crystal structure of the chemotaxis receptor methyltransferase CheR suggests a conserved structural motif for binding S–Adenosylmethionine," *Structure* 5, 545–558, 1997.

Gong, W. et al. "Structure of PvuII DNA–(cytosine N4) methyltransferase, an example of domain permutation and protein fold assignment," *Nucleic Acids Research* 25 (14), 2702–2715, 1997.

Kagan and Clarke, "Widespread occurrence of three sequence motifs in diverse S–Adenosylmethionine–dependent methyltransferases suggests a common structure for these enzymes," *Archives of Biochemistry and Biophysics* 310 (2), 417–427, 1994.

Pignot, M., et al., "Coupling of a Nucleoside with DNA by a Methyltransferase," Angew. Chem., Int. Ed., vol. 37, No. 20, pp. 2888–2891 (1998).

*Primary Examiner*—James O. Wilson
*Assistant Examiner*—Patrick Lewis
(74) *Attorney, Agent, or Firm*—Seed IP Law Group PLLC

(57) ABSTRACT

Aziridine derivatives of formula (I)

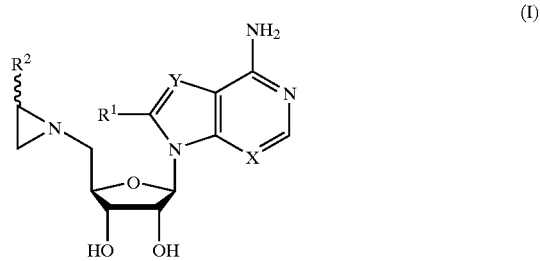

are disclosed which can be used as cofactor for S-adenosyl-L-methionine-dependent methyltransferases.

49 Claims, 8 Drawing Sheets

A

B

A

B

AZIRIDINE COMPOUNDS AND METHODS OF MAKING AND USING THEM

The present invention refers to aziridine derivatives which can be used as cofactors for methyltransferases, complexes and compositions containing these compounds and their use for modifying a target molecule.

Nonradioactively labeled nucleic acids are of considerable interest in molecular biology, because they can be used in DNA sequencing and can serve as probes for Southern/Northern blots, in situ hybridizations and colony/plaque screenings without the potential health hazards of radioactive material. Several methods are presently known in the art of covalently modifying DNA and RNA (reviewed by C. Kessler in Nonisotopic DNA Probe Techniques, L. J. Kricka (Ed.), Academic Press, San Diego, 1992, pp. 29–92). For instance, modified oligonucleotides can be obtained by solid-phase DNA or RNA synthesis and the so modified oligodeoxynucleotides can be used as primers for a DNA polymerase (P. Richterich, G. M. Church, *Methods Enzym.* 1993, 218, 187–222). If the modification can not withstand the reaction conditions used in the solid-phase synthesis, incorporation of amine or thiol groups and postsynthetical labeling of the obtained oligonucleotides with amine or thiol reactive probes is possible (D. M. Jameson, W. H. Sawyer, *Methods Enzym.* 1995, 246, 283–300). In addition, several labels may be coupled to terminal phosphate or thiophosphate residues in oligonucleotides (J.-L. Mergny et al., *Nucleic Acids Res.* 1994, 22, 920–928). Another method described in the art is the incorporation of modified deoxynucleosidetriphosphates into DNA with DNA polymerases (A. Waggoner, *Methods Enzym.* 1995, 246, 362–373) or with terminal deoxynucleotidyl transferase (L. K. Riley, M. E. Marshall, M. S. Coleman, DNA 1986, 5, 333–338; G. L. Trainor, M. A. Jensen, *Nucleic Acids Res.* 1988, 16, 11846). Furthermore, several modifications may be incorporated directly in DNA or RNA. For example, cytosine residues can be modified by activation with bisulfite followed by coupling with aliphatic amines. (R. P. Viscidi, *Methods Enzym.* 1990, 184, 600–607; D. E. Draper, L. Gold, *Biochemistry* 1980, 19, 1774–1781). In addition, other chemical reagents for labeling DNA and RNA are commercially available (FastTag, Vector, Burlingame, Calif.; Mirus Label IT, Pan Vera Corporation, Madison, Wis.). These later methods, however, do not result in quantitative and sequence specific modifications and thus complex mixtures are obtained.

Nonradioactive labeling of proteins is straightforward, because their cysteine and lysine residues react readily with a large variety of labeling reagents (M. Brinkley, *Bioconjugate Chem.* 1992, 3, 2–13; R. P. Haugland, *Handbook of Fluorescent Probes and Research Chemicals* 1996, Molecular Probes Inc., Eugene, Oreg.). However, generally proteins contain many lysine or cysteine residues and labeling often results in complex mixtures which are difficult to analyze. Thus, the specific modification of proteins is even more difficult than that of DNA and RNA. One strategy to obtain specifically labeled proteins is to engineer a protein with a single cysteine residue by means of a mutagenesis; subsequently, this cysteine residue is modified for example with a fluorescent group (G. Haran, E. Haas, B. K. Szpikowska, M. T. Mas, *Proc. Natl. Acad. Sci. USA* 1992, 89, 11764–11768).

Furthermore, unnatural amino acids may be incorporated into proteins by in vitro translation (V. W. Cornish, D. Mendel, P. G. Schultz, *Angew. Chem.* 1995, 107, 677–690; *Angew. Chem. Int. Ed. Engl.* 1995, 34, 620–630). However, this method cannot easily be carried out and it results in only a small amount of modified 4 protein.

Another possibility is the preparation of modified proteins by chemical peptide synthesis (T. W. Muir, S. B. H. Kent, *Current Opinion in Biotechnology* 1993, 4, 420427); however, it is generally restricted to the preparation of relatively short protein chains.

It is the object of the present application to overcome the drawbacks of the known methods and to provide novel compounds which enable modification of bio-molecules (for instance labeling) in a simple and effective way by the use of a methyltransferase.

This object is achieved by aziridine derivatives represented by formula (I)

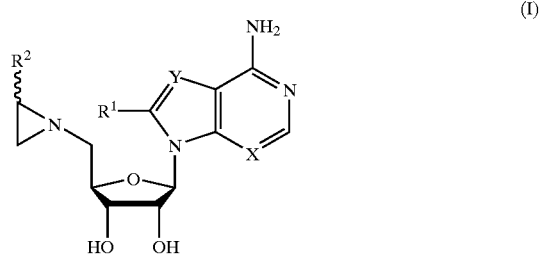

(I)

wherein X is N or CH, Y is N or —CR$^3$, R$^1$ and R$^3$ independently from each other are H, $^3$H, —NH(CH$_2$)$_n$NHR$^4$ or —NH(C$_2$H$_5$O)$_n$C$_2$H$_5$NHR$^4$, with R$^4$ being selected from fluorophores, affinity tags, crosslinking agents, chromophors, proteins, peptides, amino acids which may optionally be modified, nucleotides, nucleosides, nucleic acids, carbohydrates, lipids, PEG, transfection reagents, beads and intercalating agents and n being an integer from 1–5000, and R$^2$ is selected from H, $^3$H, —N(CH$_2$)$_n$NHR$^4$, NH(C$_2$H$_5$O)$_n$C$_2$H$_5$NHR$^4$ wherein R$^4$ and n are as defined above, —CH$_2$CH(COOH)(NH$_2$) or an electron-withdrawing group.

Figure 1:
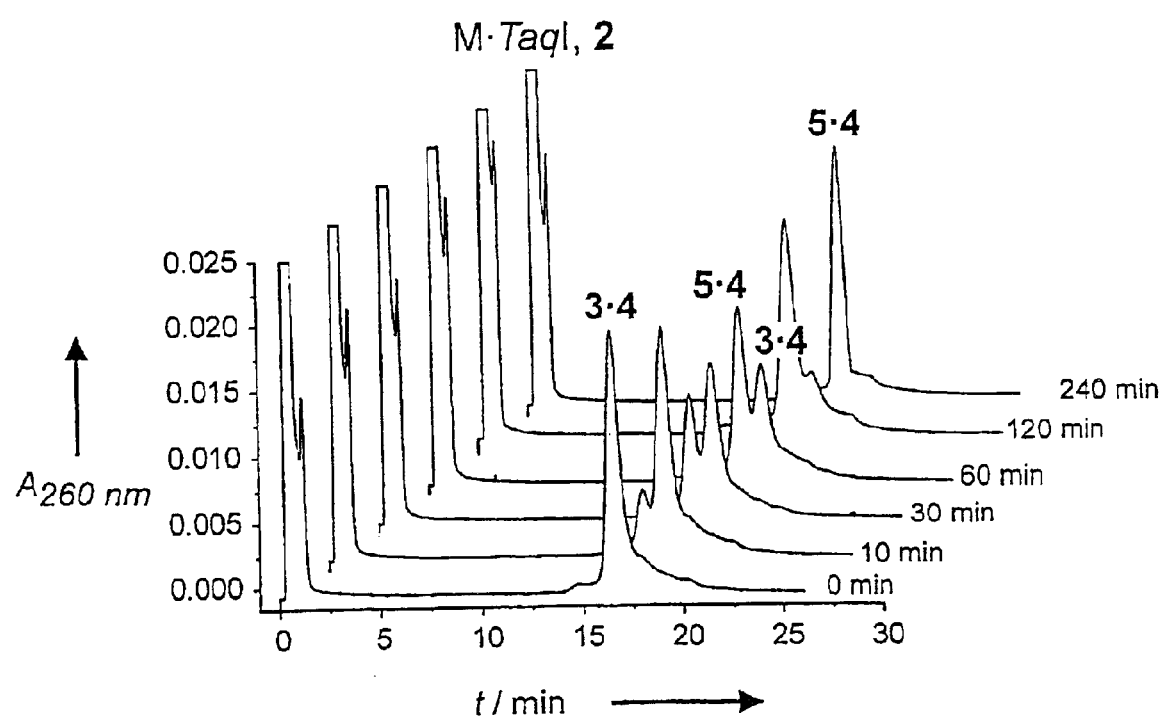
FIG. 1 shows the anion exchange chromatography of the enzyme reaction with M•TaqI of Example 1 after different incubation times.

The present invention will now be described in more detail.

S-Adenosyl-L-methionine-dependent methyltransferases (SAM-dependent methyl-transferases) are a biologically important class of enzymes. They represent about 3% of the enzymes listed in the latest version of Enzyme Nomenclature, E. C. Webb, Academic Press, San Diego, 1992. They catalyze the transfer of the activated methyl group from the cofactor S-adenosyl-L-methionine to sulfur, nitrogen, oxygen and carbon nucleophiles of small molecules, phospholipids, proteins, RNA and DNA. For instance, DNA methyltransferases catalyze the methylation of the N6 position of adenine and the $C^5$ or N4 position of cytosine within specific DNA sequences. Since restriction endonucleases are sensitive to DNA methylation, DNA methyltransferases can be used to decrease the number of restriction sites in DNA (M. Nelson, I. Schildkraut, *Methods Enzymol.* 1987, 155, e 41–48).

The reaction known to be catalyzed by SAM-dependent methyltransferases is shown schematically in the Reaction Scheme 1, where compound 1 is the cofactor S-adenosyl-L-methionine (SAM).

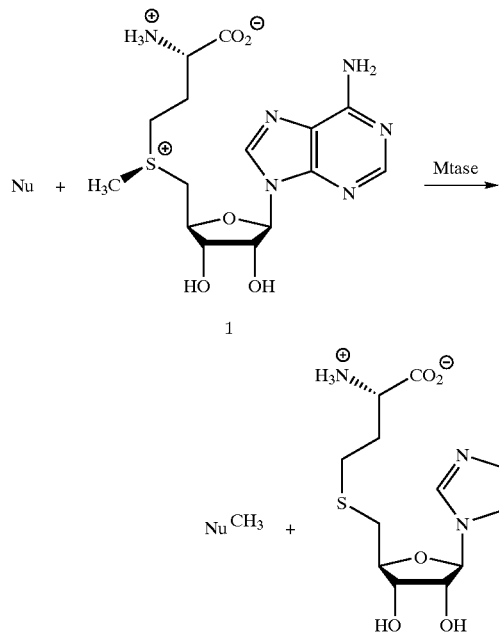

The inventors of the present application have now found that the aziridine derivatives of Formula I below serve as cofactors for SAM-dependent methyltransferases and by this way enable the transfer of groups larger than methyl.

The aziridine derivatives of the present invention are represented by Formula (I)

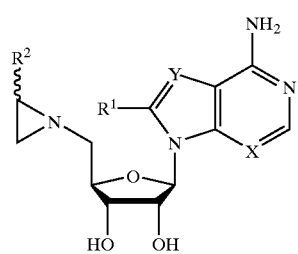

wherein X is N or CH, Y is N or —$CR^3$, $R^1$ and $R^3$ independently from each other are H, $^3H$, —$NH(CH_2)_nNHR^4$ or —$NH(C_2H_5O)_nC_2H_5NHR^4$, with $R^4$ being selected from fluorophores, affinity tags, crosslinking agents, chromophors, proteins, peptides, amino acids which may optionally be modified, nucleotides, nucleosides, nucleic acids, carbohydrates, lipids, PEG, transfection reagents, beads and intercalating agents and n being an integer from 1–5000, and $R^2$ is selected from H, $^3H$, —$N(CH_2)_nNHR^4$, —$NH(C_2H_5O)_nC_2H$ $NHR^4$ wherein $R^4$ and n are as defined above, —$CH_2CH(COOH)(NH_2)$ or an electron-withdrawing group.

Preferred electron-withdrawing groups are —$CH_{3-p}R^5_p$ (wherein p=1, 2 or 3 and each $R^5$ is independently selected from fluorine, chlorine, bromine and iodine, preferably fluorine and chlorine), —C≡N and —$C(O)R^6$ (wherein $R^6$ is an alkoxy group, hydroxy or an amino group which may be mono- or di-substituted with $C_1$–$C_{10}$ alkyl or $C_6$–$C_{10}$ aryl).

It is preferred that only one of $R^1$, $R^2$ and $R^3$ is —$NH(CH_2)_nNHR^4$ or —$NH(C_2H_5O)_nC_2H_5NHR^4$. In preferred compounds X and/or Y is N; especially preferred are compounds wherein X and Y both are N.

In the group —$NH(CH_2)_nNHR^4$ n preferably is an integer from 2 to 20, especially preferred n=3, 4 or 5.

In the group —$NH(C_2H_5O)_nC_2H_5NHR^4$ n preferably is an integer from 1 to 250; more preferred n is an integer from 1 to 20.

The term fluorophore as used herein is a chemical entity in which the electrons can be excited with light of a certain energy and photons with lower energy are emitted afterwards.

In preferred compounds of the present invention $R^1$ and $R^2$ are each H or $^3H$ and X is N.

If at least one of $R^1$, $R^2$ and $R^3$ is —$NH(CH_2)_nNHR^4$ or —$NH(C_2H_5O)_nC_2H_5NHR^4$, $R^4$ is selected from fluorophores, affinity tags, cross-linking agents, chromophors, proteins (including antibodies and enzymes), peptides, amino acids, modified amino acids, nucleotides, nucleosides, nucleic acids, carbohydrates, lipids, PEG, transfection reagents (including polyethyleneimine, macromolecules, dendrimers), beads (e.g. those consisting of agarose, silica, nitrocellulose, cellulose, acrylamide, latex, polystyrene, polyacrylate, polymethacrylate, polyethylene polymers, glass particles, silicates, metal oxides or combinations thereof), intercalating agents (including ethidium bromide, psoralene and derivatives thereof). Preferred fluorophores are BODIPY, coumarin, dansyl, fluorescein, mansyl, pyrene, rhodamine, Texas red, TNS and cyanine fluorophores like Cy2, Cy3, Cy3.5, Cy5, Cy5.5 and Cy7; derivatives of these fluorophores can also be used. An especially preferred value for $R^4$ is dansyl.

If $R^4$ is an affinity tag, it is preferably a peptide tag, biotin, digoxygenin or dinitrophenol; useful peptide tags are for example his-tag, or any tag with metal chelating properties which can be used in IMAC (Immobilized Metal Affinity Chromatography), strep-tag, flag-tag, c-myc-tag, epitopes, or gluthatione.

Useful crosslinking agents are for example maleimide, iodacetamide, derivatives thereof, aldehyde derivatives and photocrosslinking agents. Examples for photocrosslinking agents are arylazide, diazo-compounds and benzophenone compounds.

N-Adenosylaziridine (compound 2) can for instance be synthesized in a one-step reaction by nucleophilic substitution of the tosylate group of 5'-tosyladenosine with aziridine (see Reaction Scheme 2 below).

Reaction Scheme 2

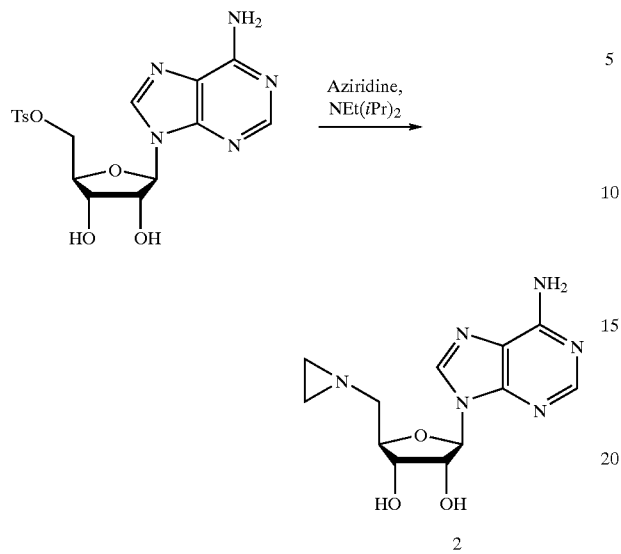

Reaction Scheme 3 shows the reaction catalyzed by a methyltransferase (MTase) using the natural cofactor 1 and on the other hand using the new cofactor 2 according to the present invention.

Reaction Scheme 3

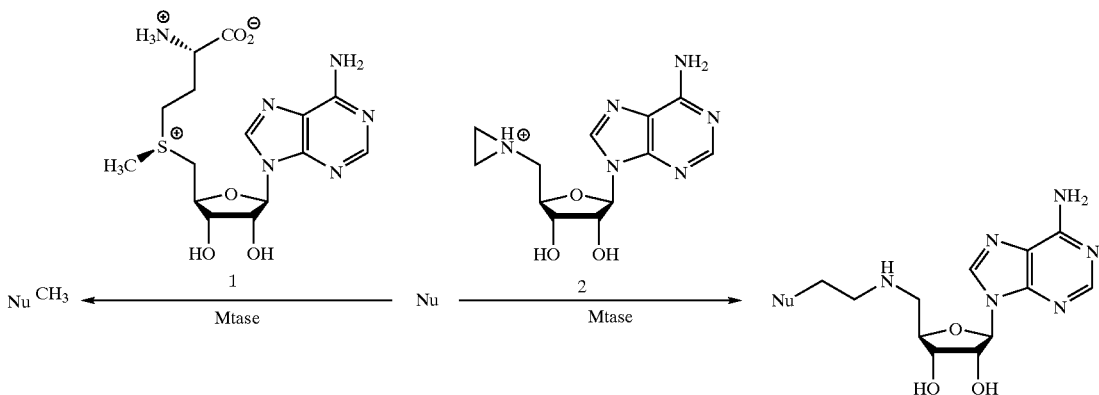

In Reaction Scheme 4, lower, the modification of a short duplex oligodeoxynucleotide (3•4), consisting of a plus strand oligodeoxynucleotide (5'-GCCGCTCGATGCCG-3', 3; SEQ ID NO:1) and a complementary minus strand oligodeoxynucleotide (5'-CGGCATCGA$^{Me}$ GCGGC-3', 4; SEQ ID NO:2) with the protonated cofactor analogue 2 containing aziridine by the use of the adenine-specific DNA methyltransferase from Thermus aquaticus (M•TaqI) is shown. The complementary minus strand oligodeoxynucleotide 4 was chosen to contain N6-methyladenine-1-β-D-2'-deoxynucleoside ($A^{Me}$), which can not be further methylated by M•TaqI. M•TaqI usually catalyzes methyl group transfer from the natural cofactor 1 to the exocyclic amino group of adenine within the double-stranded 5'-TCGA-3' DNA sequence (Scheme 4, upper) (M. McClelland Nucleic Acids Res. 1981, 9, 6795–6804).

The structure of the reaction product 5.4 can for instance be verified by reversed phase HPLC-coupled electrospray ionization mass spectrometry (RP-HPLC/ESI-MS).

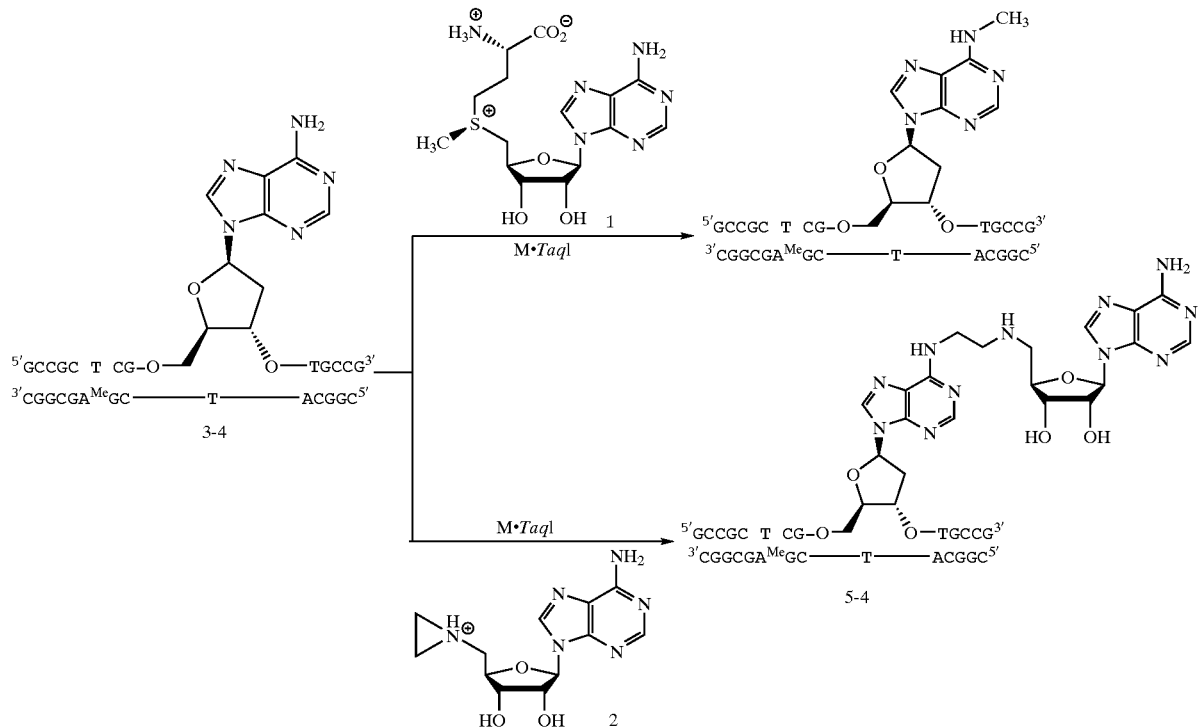

Reaction Scheme 4

Experimental results prove that with the unnatural cofactor 2 the non-methylated plus strand 3, which contains an adenine at the target position within the 5'-TCGA-3' recognition sequence of M•TaII, is modified quantitatively. Our observation that strand 4, which contains N6-methyladenine at the other target position and an adenine outside the recognition sequence, is not modified, demonstrates that the sequence specificity of M•TaqI is not altered with the new cofactor 2. In addition, enzymatic fragmentation of the product duplex 5.4 followed by reversed-phase HPLC analysis yielded an additional compound besides the natural nucleosides dC, dA, dG, T, and $dA^{Me}$. This additional compound was isolated and detected as positively charged ion at m/z 544.6 by electrospray ionization mass spectrometry. The observed mass is identical with the calculated molecular mass of a protonated, with N-adenosylaziridine modified 2'-deoxyadenosine. This result demonstrates that only the target adenine in the plus strand 3 is modified. Thus, the M•TaqI-catalyzed coupling of the new cofactor 2 with DNA is quantitative, sequence- and base-specific.

The present invention, however, is not restricted to M•TaqI but the C5-cytosine-specific DNA methyltransferase *Haemophilus haemolyticus* (M•HhaI) and other methyltransferases normally using S-adenosyl-L-methionine (SAM) as cofactor can also be used. This is readily demonstrated by the modification of the duplex oligodeoxynucleotide 6•7 using M•HhaI (the sense and antisense strands depicted in Scheme 5 are SEQ ID NOs:3 and 4, respectively). Naturally, M•HhaI catalyzes the transfer of the activated methyl from SAM to the carbon atom at the 5 position of the first cytosine within the double stranded 5'-GCGC-3' DNA sequence (Scheme 5, upper). Experimental results prove that M•HhaI also accepts the new cofactor 2 and catalyzes its coupling to the duplex oligodeoxynucleotide 6•7 (Scheme 5, lower). Like the M•TaqI-catalyzed reaction, the M•HhaI-catalyzed coupling is quantitative.

Reaction Scheme 5

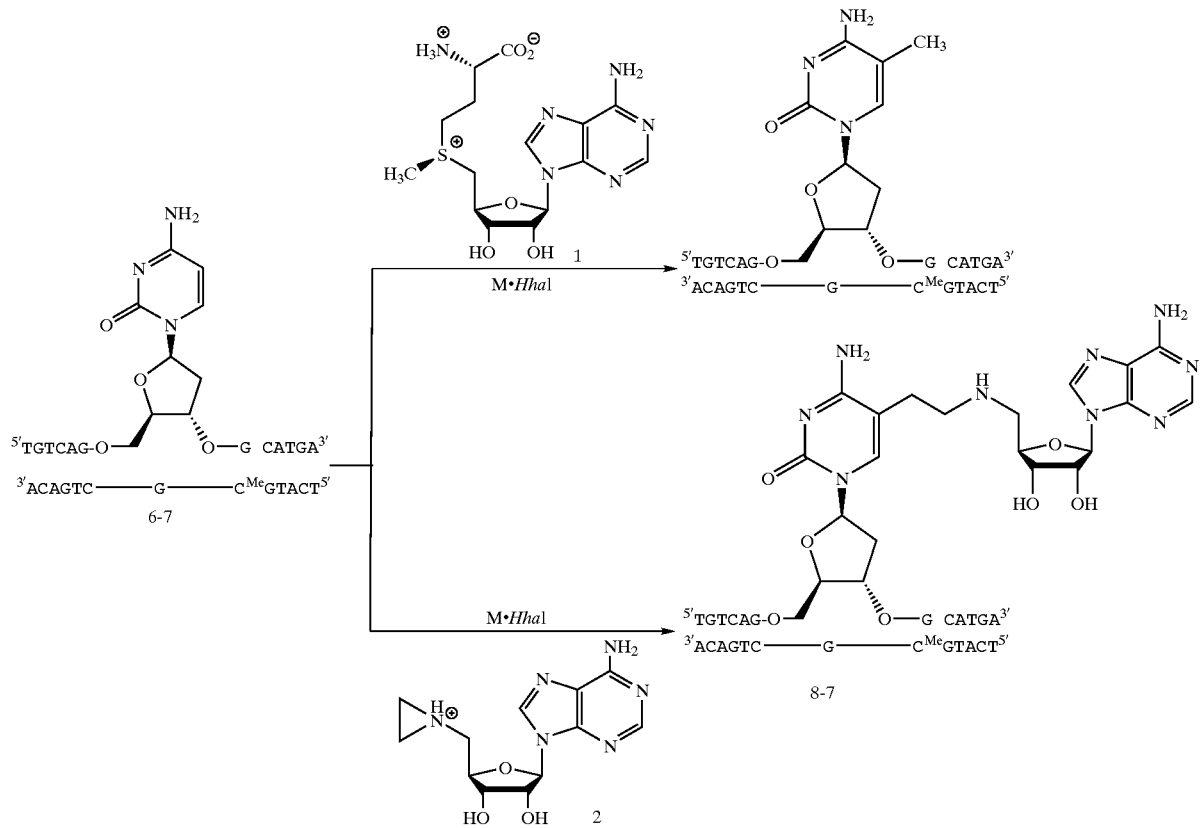

This application for the first time describes the transfer of a group larger than a methyl group catalyzed by two different S-adenosyl-L-methionine-dependent methyltransferase. Since the transfer of for instance compound 2 introduces a unique secondary amino group into DNA, subsequent labeling reactions with amine reactive probes should be feasible. Thus, site-specific introduction of fluorescent, chemiluminescent or other reporter groups is possible. Alternatively, the new fluorescent cofactor 9 where $R^1$ is $-NH(CH_2)_4NHR^4$, $R^2$ is H, Y is N and $R^4$ is the fluorescent dansyl group can be used to obtain sequence-specifically labeled DNA directly. This fluorescent N-adenosylaziridine derivative contains the reactive aziridine group at the 5' position, the adenosyl moiety, which serves as the molecular anchor for the cofactor binding of methyltransferases, and the fluorescent dansyl group (label), which is attached to the 8 position via a flexible linker. The synthesis of this new fluorescent cofactor 9 is illustrated in Scheme 6. Reaction of 8-bromo-2',3'-O-isopropylidene adenosine with 1,4-diaminobutane yields the protected adenosine derivative 10 with an aminolinker at the 8 position. Transient protection of the 5' hydroxy group with trimethylchlorosilan, coupling of dansyl chloride with the primary amine and removal of the 5' hydroxyl protecting group leads to the protected fluorescent adenosine derivative 11. Reaction of 11 with mesylchloride yields the mesylate 12. Removal of the isopropylidene group of 12 under acidic conditions leads to the fluorescent adenosine derivative 13 which is reacted with aziridine to give the new fluorescent cofactor 9.

Reaction Scheme 6

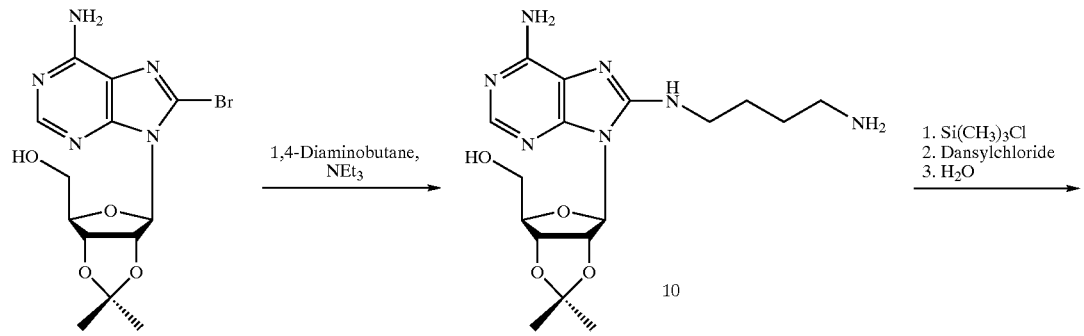

-continued

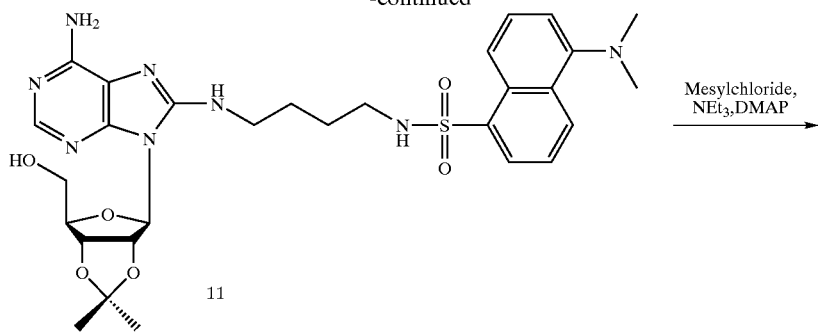

11

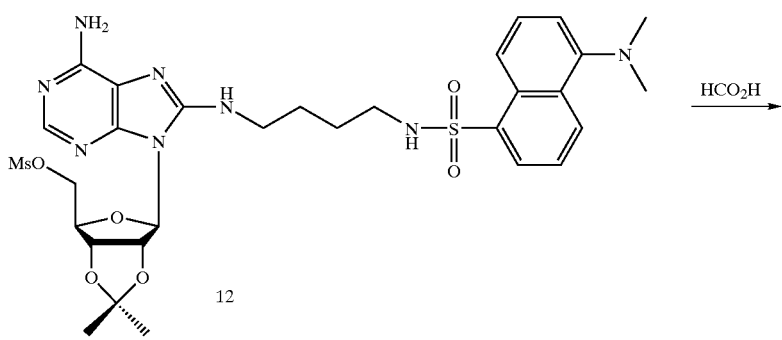

12

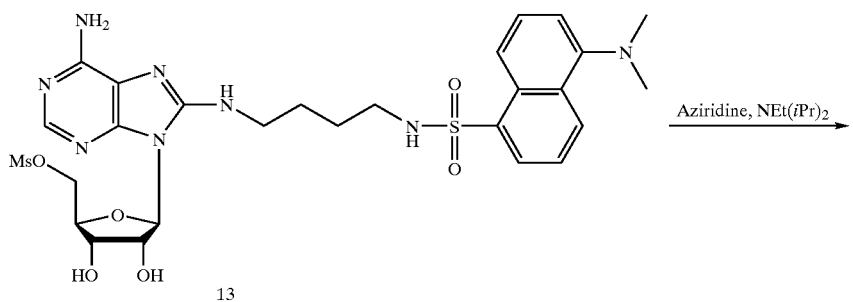

13

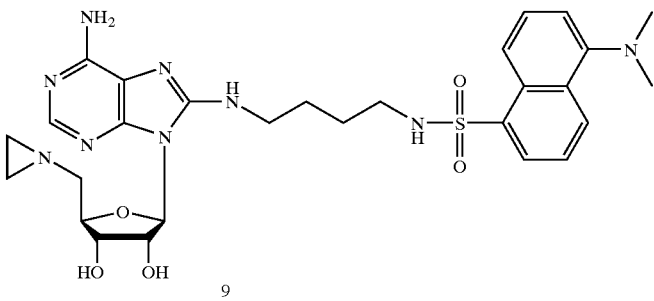

9

The M•TaqI-catalyzed coupling of the new fluorescent cofactor 9 with the duplex oligodeoxynucleotide 3•4 (Scheme 7; sense and antisense strands are SEQ ID NOs:1 and 2, respectively) was followed by anion exchange chromatography. After proteolytic fragmentation of the formed M•TaqI-DNA complex the fluorescently labeled duplex oligodeoxynucleotide 14•4 is formed. The structure of the product 144 was verified by enzymatic fragmentation followed by reversed-phase HPLC. The analysis revealed besides the natural nucleosides dC, dA, dG T, and dA$^{Me}$ an additional fluorescent compound, which eluted with a much higher retention time than the natural nucleosides demonstrating its hydrophobic nature. This additional fluorescent compound was isolated and detected as positively charged ion at m/z 863.1 by electrospray ionization mass spectrometry. The observed mass is in good agreement with the calculated molecular mass of 863.4 for a protonated, with 9 modified 2'-deoxyadenosine. Thus, the coupling reaction of the new fluorescent cofactor 9 with DNA catalyzed by M•TaqI is quantitative and base-specific.

Reaction Scheme 7

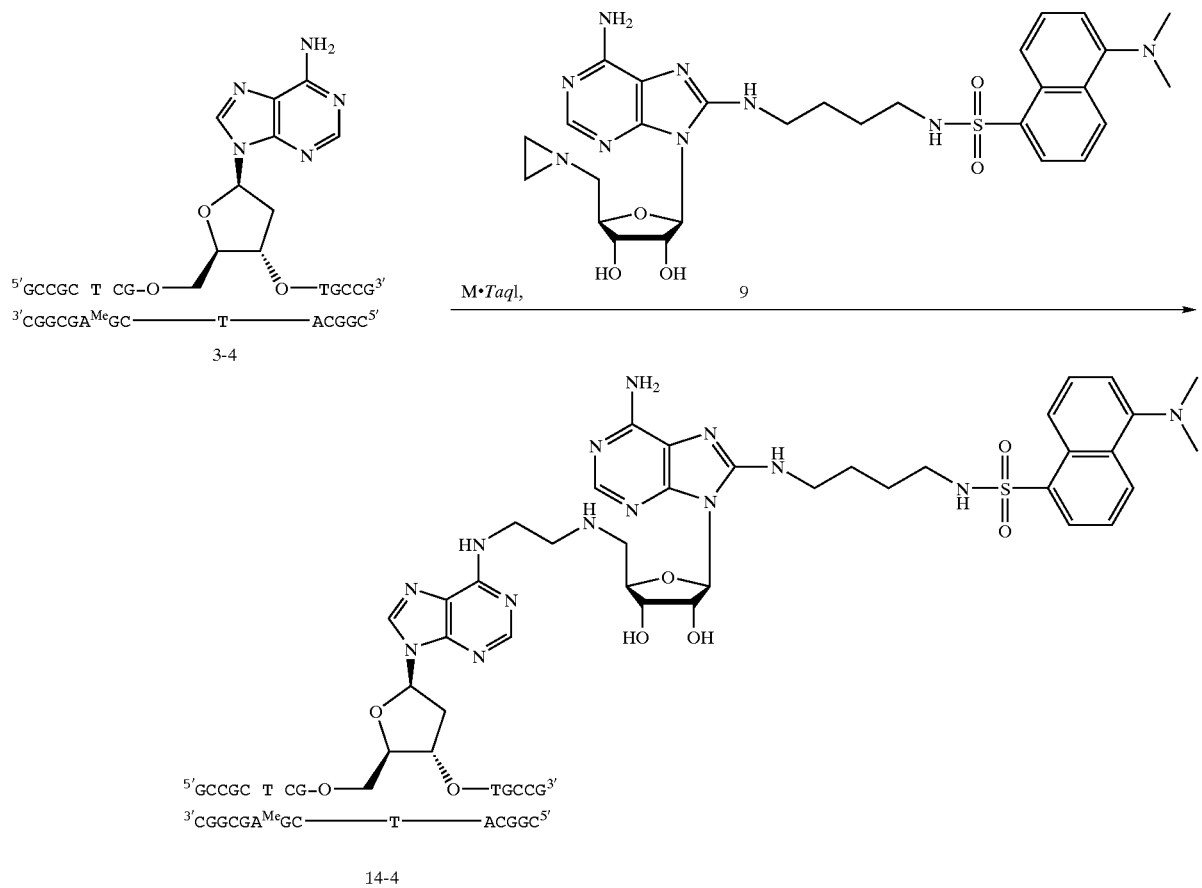

The present invention can also be used to label larger DNA molecules. This is proved by labeling of the plasmid pUC19 (2,686 base pairs) with the new fluorescent cofactor 9 and M-TaqI. The labeling reaction was analyzed by anion exchange chromatography after different incubation times. While the chromatograms using UV detection did not significantly change, the chromatograms using fluorescence detection clearly showed an increase of the fluorescence signal with the incubation time. The UV signal and the fluorescence signal superimpose and indicate that the starting material pUC19 (UV absorption only) and fluorescently labeled pUC19 (UV absorption and fluorescence) elute with the same retention time. In a parallel control experiment without M•TaqI no fluorescence signal corresponding to fluorescently labeled pUC19 was observed. This result demonstrates that the labeling reaction is in fact M-TaqI-catalyzed. Interestingly, the fluorescent nucleoside 9 also function as a cofactor for M•HhaI. Analysis of the M•HhaI-catalyzed coupling reaction between fluorescent nucleoside 9 and pUC19 by anion exchange chromatography shows that fluorescently labeled 2 pUC19 is also produced and that no labeling occurs without M•HhaI.

The three-dimensional structures of, several methyltransferases in complex with the natural cofactor (N-6-adenine DNA methyltransferase M•TaqI: J. Labahn, J. Granzin, G. Schluckebier, D. P. Robinson, W. E. Jack, l. Schildkraut, W. Saenger, Proc. Natl. Acad. Sci. USA 1994, 91, 10957–10961; N6-adenine DNA methyltransferase DpnM: P. H. Tran, Z. R. Korszun, S. Cerritelli, S. S. Springhorn, S. A. Lacks, Structure 1998, 6, 1563–1575; C5-cytosine DNA methyltransferase M•HhaI: S. Klimasauskas, S. Kumar, R. J. Roberts, X. Cheng, Cell 1994, 76, 357–369; N4-cytosine DNA methyltransferase M•PvuII: W. Gong, M. O'Gara, R. M. Blumenthal, X. Cheng, Nucleic Acids Res. 1997, 25, 2702–2715; N6-adenine RNA methyltransferase ErmC': D. E. Bussiere, S. W. Muchmore, C. G. Dealwis, G. Schluckebier, V. L. Nienaber, R. P. Edalji, K. A. Walter, U.S. Ladror, T. F. Holzman, C. Abad-Zapatero, Biochemistry 1998, 37, 7103–7112; mRNA 2'-O-nucleoside methyltransferase VP39: A. E. Hodel, P. D. Gershorn, X. Shi, F. A. Quiocho, Cell 1996, 85, 247–256; protein methyltransferase CheR: S. Djordjevic, A. M. Stock, Structure 1997, 5, 545–558) indicate that the 8 position of the adenine ring of the natural cofactor is at least partly accessible to the solvent, and thus is suitable for the attachment of an additional group without strongly interfering with the cofactor binding of these methyltransferases. In some methyltransferases the 7 position of the adenine ring of the natural cofactor is even more exposed to the solvent and, therefore, might be the preferred position of choice for the attachment of additional groups (Y in Formula I) for these methyltransferases. In addition, the three-dimensional structure of the catechol O-methyltransferase COMT in complex with the natural cofactor (J. Vidgren, L. A. Svensson, A. Liljas, Nature 1994, 368, 354–358) shows that the adenine ring of the natural cofactor is buried within the cofactor binding pocket. Here, the attachment of an additional group at the 5' aziridine ring ($R^2$ in Formula I) seems most compatible with the cofactor binding of this methyltransferase. Thus, the new cofactors with modifications at the 8-position of the adenine ring ($R^1$ in Formula I), at the 7 position of the adenine ring (Y in Formula I) or at the 5' aziridine ring ($R^2$ in Formula I)

can be used to obtain a wide variety of site-specifically labeled biomolecules.

The methyltransferases useful in the present invention normally transfer the methyl group of SAM onto a nucleic acid molecule like DNA or RNA, onto a polypeptide, a protein, an enzyme or a small molecule. An overview on SAM-dependent methyltransferases is for instance given by R. M. Kagan and S. Clarke in Archives of *Biochemistry and Biophysics* 1994, 310, 417–427. This article also gives a list of small molecule O-methyltransferases and small molecule N-methyltransferases which include for example catechol O-methyltransferase and glycine N-methyl-transferase.

Particularly preferred for use in the present invention are methyltranferases which methylate DNA, especially, those which are part of a restriction modification system of a bacterium and methyltransferases which methylate proteins at distinct amino acids.

The present invention not only refers to the aziridine derivatives themselves but also to the complex of such a derivative and a methyltransferase as well as pharmaceutical and diagnostic compositions comprising an aziridine derivative of the present invention or a complex thereof with a methyltransferase.

The aziridine derivatives of the present invention can be used for modifying a target molecule (e.g. DNA or fragments thereof, RNA or fragments thereof, hybrids of DNA and RNA, polypeptides, for instance proteins of fusion proteins comprising a methylation site, synthetic polymers and small molecules like lipids). This can be done by transferring an aziridine derivative of the present invention or a part thereof onto the target molecule by means of a methyltransferase.

The present invention will now be further illustrated by the following examples.

EXAMPLE 1

1. Synthesis of N-Adenosylaziridine, Compound 2 (Scheme 2).

Dry aziridine (S. Gabriel, *Chem. Ber.* 1888, 21, 2664–2669; S. Gabriel, R. Stelzner, *Chem. Ber.* 1895, 28, 2929–2938) (360 μl, 7.2 mmol) was added slowly to a suspension of 5'-tosyladenosine (100 mg, 0.24 mmol, Aldrich) in N-ethyldiisopropylamine (125 μl, 0.7 mmol) under an argon atmosphere, and the resulting solution was stirred at room temperature for three days. Any aziridine remaining was removed under reduced pressure, and the crude reaction product was dissolved in water (1 ml) and neutralized with acetic acid (1 M). The solution (100 μl at a time) was injected onto a reversed-phase HPLC column (Hypersil-ODS, 5 μm, 120A. 250×10 mm, Bischoff, Leonberg, Germany), and the product was eluted with a linear gradient of acetonitrile (7–10% in 30 min, 2 ml/min) in triethylammonium hydrogencarbonate buffer (0.1 M, pH 8.4). Fractions containing product (retention time 11.3 min, UV detection at 259 nm) were combined, concentrated by lyophilization to 5.5 ml (10.5 mM, using ?. =260, E=15400 of adenosine) and stored at −80° C. Yield: 0.058 mmol (24%). For further characterization an aliquot was completely lyophilized to afford compound 2 as a white solid.

$^1$H NMR (500 MHz, D$_2$O): δ=1.49–1.40 (m, 2H; aziridine-H), 1.85–1.74 (m, 2H; aziridine-H), 2.74 and 2.68 (AB part of ABX-spectrum, $^3$J=4.3, 6.6 Hz, $^2$J=13.3 Hz, 2H; 5'-Ha, 5'-H$_b$), 4.35 (ddd=dt, $^3$J=4.6, 4.6, 6.7 Hz, 1H; 4'-H), 4.46 (dd=t, $^3$J=5.1 Hz, 1H; 3'-H), 4.84 (dd=t, $^3$J=5.3 Hz, 1H; 2'-H), 6.13 (d, $^3$J=5.0 Hz, 1H; 1'-H), 8.30 (s, 1H; 8-H), 8.36 (s, 1H; 2-H).

FAB-MS (thioglycolic acid): m/z (%): 293 (100) [M$^+$+H], 250 (4) [M$^+$-C$_2$H$_4$N], 178 (11) [B$^+$+C$_2$H$_4$O], 167 (34), 165 (5), 164 (5) [B$^+$+CH$_2$O], 158 (36) [M$^+$−B], 149 (78), 136 (91) [BH$_2$+], 102 (23); B=deprotonated adenine.

2. Synthesis and Purification of Oligodeoxynucleotides.

Oligodeoxynucleotides 3, 4, 6 and 7 were synthesized on an Applied Biosystems 392 DNA/RNA synthesizer, using standard P-cyanoethyl phosphoramidite chemistry. Syntheses were performed "trityl on" and oligodeoxynucleotides were purified by reversed-phase HPLC. After detritylation with acetic acid (80%), the oligodeoxynucleotides were further purified by reversed-phase HPLC ("trityl off") and desalted by gel filtration. The duplex oligodeoxynucleotides 3.4 and 67 were formed by incubatng equal molar amounts of the complementary strands in buffer (20 mM Tris acetate, 50 mM potassium acetate, 10 mM magnesium acetate, pH 7.9 for 3.4 and 10 mM Tris chloride, 50 mM sodium chloride, 0.5 mM EDTA, pH 7.4 for 67) at 95° C. (2 min) followed by slow cooling (2 h) to room temperature.

3. Enzyme Reactions 3.1 Enzyme Reaction With the N6-adenine DNA methyltransferase M•TaqI.

The DNA methyltransferase M•TaqI free of cofactor was prepared as described before (B. Holz, S. Klimasauskas, S. Serva, E. Weinhold, *Nucleic Acids Res.* 1998, 26, 1076–1083). The enzyme-catalyzed reaction was carried out in a mixture (500 μl) of M•TaqI (5 nmol, 10 μM), duplex oligodeoxynucleotide 3.4 (5 nmol, 10 μM), compound 2 (500 nmol, 1 mM), Tris acetate (20 mM, pH 6,0), potassium acetate (50 mM), magnesium acetate (10 mM) and Triton X-100 (0.01%) at 37°C. The progress of the reaction was monitored by anion exchange chromatography. Aliquots (50 μl) of the reaction mixture were withdrawn after different incubation times, mixed with an urea solution (100 μl, 6 M) and injected onto an anion exchange column (Poros 10 HQ, 10 μm, 4.6×100 mm, PerSeptive Biosystems, Germany). Compounds were eluted with aqueous potassium chloride (0.5 M for 5 min, followed by a linear gradient to 1 M in 30 min, 4 ml/min) in Tris chloride buffer (10 mM, pH 7.6). The chromatograms of the anion exchange chromatography after different incubation times are shown in FIG. 1.

Analysis of the product duplex oligodeoxynucleotide 5.4 by reversed-phase HPLC-coupled electrospray ionization mass spectrometry: RP-HPLC/ESI-MS was performed with an ion-trap mass spectrometer (LCQ, Finnigan MAT, Germany) equipped with a micro HPLC system (M480 and M300, Gynkotek, Germany). The product duplex oligodeoxynucleotide 5.4 was purified by anion exchange chromatography (see above) and desalted by repeated addition of water and ultrafiltration (Microsep 3K, Pall Filtron, Northborough, Mass., USA). A solution of purified and desalted 5.4 was injected onto a capillary column (Hypersil-ODS, 3 μm, 150×0.3 mm, LC Packings, Amsterdam, Netherlands) and eluted with a linear gradient of acetonitrile (7–10% in 10 min, followed by 10–70% in 30 min, 150 μl/min) in triethylammonium acetate buffer (0.1 M, pH 7.0). The RP-HPLC/ESI mass spectra shown in FIG. 2A was obtained in the negative ion mode using standard conditions. The chromatogram obtained by observing the total ion current is given in the inset of FIG. 2A.

Analysis of the product duplex oligodeoxynucleotide 5.4 by electrospray ionization mass spectrometry using direct infusion: The ESI mass spectrum shown in FIG. 2B was acquired using a double focussing sector field mass spectrometer MAT 90 (Finnigan MAT, Germany) equipped with an ES II electrospray ion source in the negative ion mode. Desalted 5.4 (aqueous solution) and a liquid sheath flow (2-propanol) were delivered using a Harvard syringe pump (Harvard Apparatus, USA). The inset in FIG. 2B shows an expansion of the signal for the [5–6H]$^{6-}$ ion with isotopic resolution.

Figure 2:
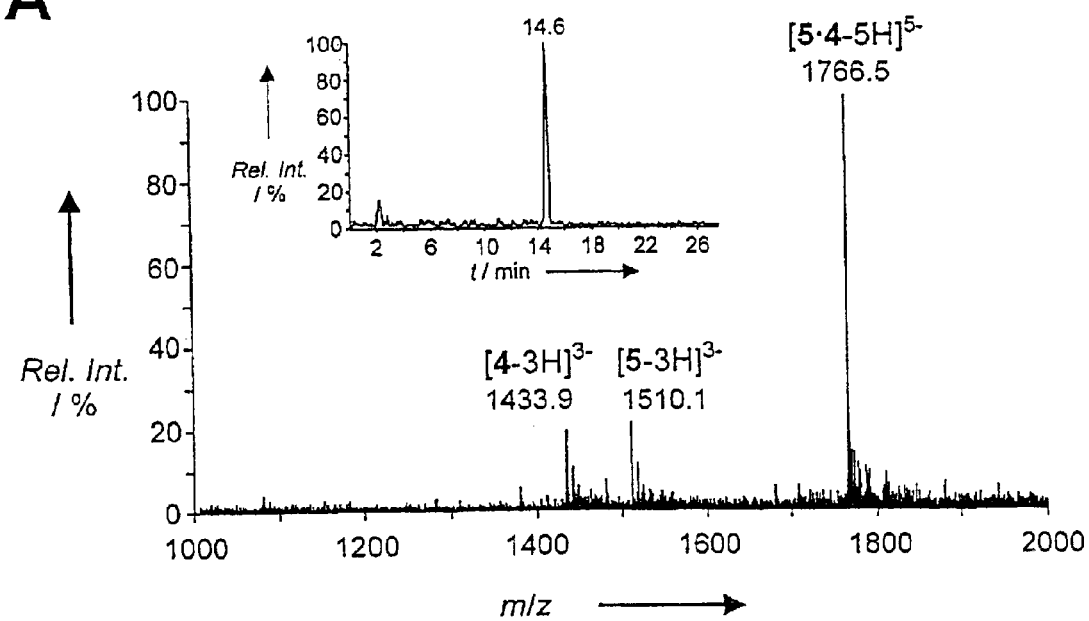
FIG. 2A shows the RP-HPLC/ESI mass spectrum of the product duplex oligodeoxynucleotide 5.4 of Example 1 eluted after 14.6 min.
FIG. 2B shows the ESI mass spectrum of the product 5.4 of Example 1 obtained by direct infusion.
Figure 2:
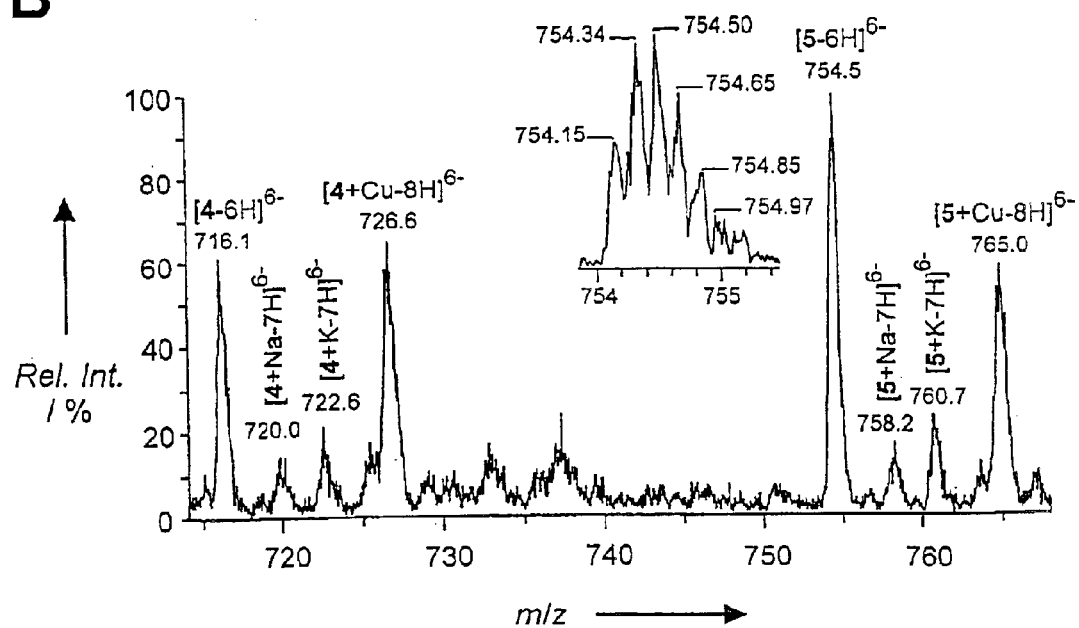

The molecular weights of oligodeoxynucleotides observed in the electrospray mass spectra from FIGS. 2A and 2B are summarized in Table 1. In addition, the observed molecular weights of the educt oligodeoxynucleotides are given.

TABLE 1

| Compound | Charge | (m/z)$_{expt}$ | M$_{expt}$ | M$_{calcd}$ |
|---|---|---|---|---|
| 1) RP-HPLC/ESI-MS | | | | |
| 5.4 | 5– | 1766.5 | 8837.5 | 8836.9 |
| 5 | 3– | 1510.1 | 4533.3 | 4533.1 |
| 4 | 3– | 1433.9 | 4304.7 | 4303.8 |
| 3.4 | 5– | 1708.0 | 8545.0 | 8544.6 |
| 3 | 3– | 1412.7 | 4241.1 | 4240.8 |
| 2) ESI-MS by direct infusion | | | | |
| 5 | 6– | 754.5 | 4533.1 | 4533.1 |
| 4 | 6– | 716.1 | 4302.7 | 4303.8 |
| 3 | 6– | 705.7 | 4240.3 | 4240.8 |

Analysis of the product duplex oligodeoxynucleotide 5.4 by enzymatic fragmentation: Purified and desalted 5.4 (0.25 OD at 260 nm) was dissolved in potassium phosphate buffer (10 mM, pH 7.0, 100 Of) containing magnesium chloride (10 mM), DNase I (1.2 U), phosphodiesterase from *Crotalus durissus* (0.018 U), phosphodiesterase from calf spleen (0.024 U) and alkaline phosphatase (6 U) and incubated at 37° C. for 24 h. An aliquot (50 µl) was injected onto a reversed-phase HPLC column (Hypersil-ODS, 5 µm, 120 Å, 250×4.6 mm, Bischoff, Leonberg, Germany), and the products were eluted with a linear gradient of acetonitrile (0–10.5% in 30 min, 1 ml/min) in triethylammonium acetate buffer (0.1 M, pH 7.0). The RP-HPLC analysis of the digest revealed besides dC, dA, dG, T, and dA$^{Me}$ an additional compound eluting between T and dA$^{Me}$. This additional compound was isolated and detected as positively charged ion at m/z 544.6 by ESI-MS (LCQ connected to a nano-electrospray ion source, Finnigan MAT, Germany). The observed mass is identical with the calculated molecular mass of a protonated, with N-adenosylaziridine modified 2'-deoxyadenosine.

3.2 Enzyme Reaction With the C5-cytosine dNA methyltransferase m•HhaI.

Figure 3:
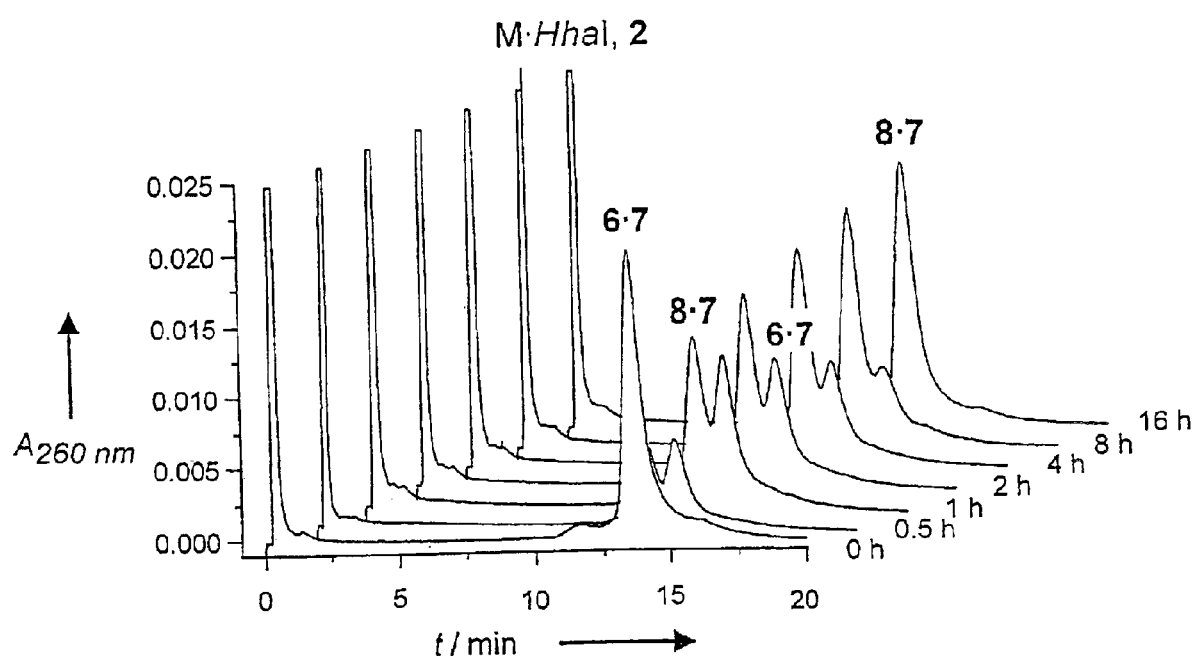
FIG. 3 shows the anion exchange chromatography of the enzyme reaction with M•HhaI of Example 1 after different incubation times.

The DNA methyltransferase M•HhaI free of cofactor was prepared as described before (B. Holz, S. Klimasauskas, S. Serva, E. Weinhold, *Nucleic Acids Res.* 1998, 26, 1076–1083). The enzyme-catalyzed reaction was carried out in a mixture (500 µl) of M•HhaI (5 nmol, 10 µM), duplex oligodeoxynucleotide 6•7 (5 nmol, 10 µM), compound 2 (500 nmol, 1 mM), Tris chloride (10 mM, pH 7.4), sodium chloride (50 mM), EDTA (0,5 mM) and Triton X-100 (0.01%) at 25° C. The progress of the reaction was monitored by anion exchange chromatography. Aliquots (50 µl) of the reaction mixture were withdrawn after different incubation times, and injected onto an anion exchange column (Poros 10 HQ, 10 µm, 4.6×100 mm, PerSeptive Biosystems, Germany). Compounds were eluted with aqueous potassium chloride (0 M for 5 min, followed by a linear gradient to 0.5 M in 5 min and to 1 M in 30 min, 4 ml/min) in Tris chloride buffer (20 mM, pH. 7.6). The chromatograms of the anion exchange chromatography after different incubation times are shown in FIG. 3.

Figure 4:
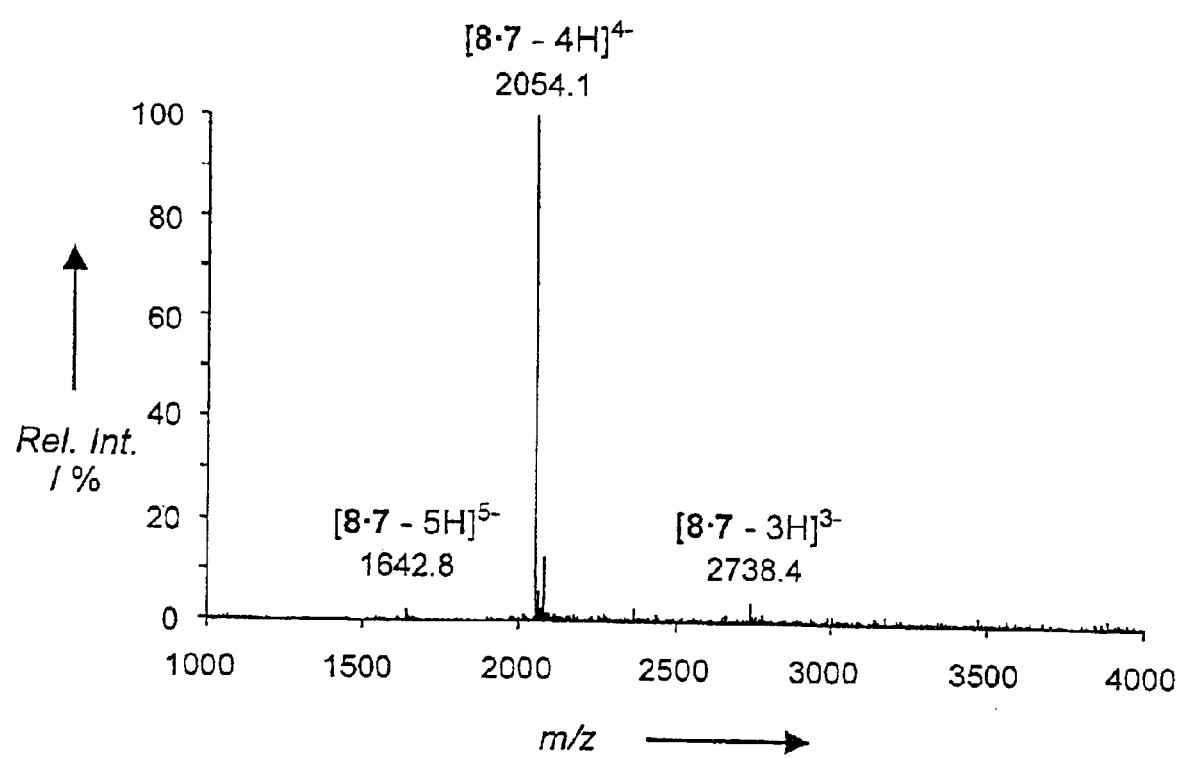
FIG. 4 shows the RP-HPLC/ESI mass spectrum of the product duplex oligodeoxynucleotide 8.7 of Example 1.

Analysis of the product duplex oligodeoxynucleotide 8.7 by reversed-phase HPLC-coupled electrospray ionization mass spectrometry: RP-HPLC/ESI-MS was performed as described before for the analysis of 5.4 (see example 1, 3.1). The obtained RP-HPLC/ESI mass spectrum is shown in FIG. 4 and the observed molecular weights of oligodeoxynucleotides are summarized in Table 2.

TABLE 2

| Compound | Charge | (m/z)$_{expt}$ | M$_{expt}$ | M$_{calcd}$ |
|---|---|---|---|---|
| 8.7 | 3– | 2738.4 | 8220.2 | 8215.5 |
| 8.7 | 4– | 2054.1 | 8220.4 | 8215.5 |
| 8.7 | 5– | 1642.8 | 8219.0 | 8215.5 |

Analysis of the product duplex oligodeoxynucleotide 87 by enzymatic fragmentation: Enzymatic fragmentation of 8.7 was performed as described before for 54 (see example 1, 3.1). The RP-HPLC analysis of the digest revealed besides dC, dC$^{Me}$, dA, dG, T an additional compound eluting before dC.

EXAMPLE 2

1. Synthesis of a Fluorescent N-adenosylaziridine Derivative, Compound 9 (Scheme 6).

1.1 8-Amino[1"-(4"-aminobutyl)]-2',3'-O-isopropylidene adenosine, Compound 10.

To a solution of 8-bromo-2',3'-O-isopropylene adenosine (M. Ikehara, H. Tada, M. Kaneko, Tetrahedron 1968, 24, 3489–3498) (628 mg, 1.6 mmol) in dry DMSO (10 ml) under an argon atmosphere, dry triethylamine (2.26 ml, 16.3 mmol) and 1,4-diaminobutane (0.82 ml, 8.1 mmol) were added. The solution was stirred at 110° C. and the reaction progress monitored by TLC. After 4 h the solvent was removed under reduced pressure. The residue was dissolved in water (50 ml) and the pH was adjusted to 5.3 with acetic acid (0.1 M). The crude product was purified by cation exchange chromatography (Dowex 50×4 in H$^+$-form, 100 g, elution with 600 ml water and subsequently with 1000 ml 1 M potassium hydroxide). Fractions containing the product were extracted with chloroform, and the solvent was removed under reduced pressure. Yield: 639 mg (100%).

R$_f$=0.44 (butanol/acetic acid/water 3:0.75:1.25).

$^1$H NMR (500 MHz, CDCl$_3$): δ=1.33 (s, 3H; acetonide-H), 1.48–1.55 (m, 2H; linker-H), 1.61 (s, 3H; acetonide-H), 1.64–1.70 (m, 2H; linker-H), 2.66–2.73 (m, 2H; linker-H), 3.33–3.42 (m, 2H; linker-H), 3.77–3.91 (m, 2H; 5'-H), 4.28–4.30 (m, 1H; 4'-H), 4.99 (dd, $^3$J=2.7, 6.3 Hz, 1H; 3'-H), 5.08 (dd, $^3$J=4.8, 6.3 Hz, 1H; 2'-H), 5.39 (s, br., 2H; 6-NH$_2$), 6.15 (d, $^3$J=4.5 Hz, 1H; 1'-H), 6.55–6.60 (m, 1H; 8-NH), 8.10 (s, 1H; 2-H).

$^{13}$C-NMR (125.7 MHz, CDCl$_3$): δ=25.30 (q; acetonide-CH$_3$), 25.73 (t; linker-C), 27.42 (q; acetonide-CH$_3$), 29.60 (t; linker-C), 40;46 (t; linker-C), 42.69 (t; linker-C), 61.17 (t; 5'-C), 80.59 (d; 3'-C), 82.19 (d; 2'-C), 84.48 (d; 4'-C), 89.21 (d; 1'-C), 114.50 (s; acetonide-C(CH$_{32}$), 117.68 (s; 5-C), 149.49 (d; 2-C), 149.95 (s; 8-C), 151.68 (s; 4-C), 151.72 (s; 6-C).

ESI-MS: m/z (%): 394.3 (25) [M+H]$^+$, 222.3 (100) [adenine+aminobutyl+H]$^+$.

1.2 8-Amino[1"-(N"-dansyl)-4"-aminobutyl]-2',3'-O-isopropylidene adenosine, Compound 11.

To a solution of 10 (104 mg, 0,26 mmol) in dry pyridine (7 ml) under an argon atmosphere, trimethylchlorosilane (0.07 ml, 0.53 mmol) was added slowly at 0° C., and the resulting solution was stirred at room temperature for 1 h. Subsequently, dansyl chloride (103.8 mg, 0.37 mmol, in 3 ml pyridine) was added and the solution was stirred at room temperature for 4 h. The progress of the reaction was monitored by TLC, and after complete conversion the solution was treated with water (5 ml) at 0° C. The solvent was removed under reduced pressure, and the crude product was purified by column chromatography (silica gel, 40 g, elution with methylene chloride/methanol 19:1). Yield: 50 mg (30%).

R$_f$=0.54 (methylene chloride/methanol 9:1).

$^1$H-NMR (500 MHz, DMSO-d$_6$): δ=1.29 (s, 3H; acetonide-H), 1.39–1.43 (m, 2H; linker-H), 1.47–1.50 (m, 2H; linker-H), 1.53 (s, 3H; acetonide-H), 2.78–2.82 (m, 8H; linker-H and N(CH$_3$)$_2$), 3.16–3.24 (m, 2H; linker-H), 3.50–3.58 (m, 2H; 5'-H), 4.12–4.14 (m, 1H; 4'-H), 4.94 (dd, $^3$J=2.7, 6.1 Hz, 1H; 3'-H), 5.33 (dd, $^3$J=3.7, 6.1 Hz, 1H; 2'-H), 5.41–5.44 (m, 1H; 5'-OH), 6.01 (d, $^3$J=3.5 Hz, 1H; 1'-H), 6.49 (s, br., 2H; 6-NH$_2$), 6.85 (t, $^3$J=5.0 Hz, 1H; 8-NH), 7.22 (d, $^3$J=7.5 Hz, 1H; arom.-H), 7.54–7.61 (m, 2H; arom.-H), 7.87–7.90 (m, 1H; NHSO$_2$), 7.90 (s, 1H; 2-H), 8.08 (d, $^3$J=7.2 Hz, 1H; arom.-H), 8.30 (d, $^3$J=8.5 Hz, 1H; arom.-H), 8.43 (d, $^3$J=8.5 Hz, 1H; arom.-H).

$^{13}$C-NMR (125.7 MHz, DMSO-d$_6$): δ=25.42 (q; acetonide-CH$_3$), 26.00 (t; linker-C), 26.9.6 (t; linker-C), 27.33 (q; acetonide-CH$_3$), 41.92 (t; linker-C), 42.43 (t; linker-C), 45.21 (q; N(CH$_3$)$_2$), 61.40 (t; 5'-C), 81.14 (d; 3'-C), 81.50 (d; 2'-C), 85.29 (d; 4'-C), 87.85 (d; 1'-C), 113.38 (s), 115.24 (d; arom.-C), 117.24 (s), 119.29 (d; arom.-C), 123.72 (d; arom.-C), 127.92 (d; arom.-C), 128.31 (d; arom.-C), 129.26 (s), 129.48 (d; arom.-C), 136.27 (s), 148.89 (d; 2-C), 149.30 (s), 151.20 (s), 151.50 (s), 152.58 (s).

ESI-MS: m/z (%): 627.1 (100) [M+H]$^+$, 455.2 (8) [adenine+linker+dansyl+H]$^+$.

1.3 8-Amino[1"-(N"-dansyl)-4"-aminobutyl]-2',3'-O-isopropylidene-5'-O-mesyl adenosine, Compound 12.

To a solution of 11 (181 mg, 0.32 mmol) and dimethylaminopyridine (40 mg, 0.32 mmol) in dry methylene chloride (20 ml) under an argon atmosphere, dry triethylamine (1.1 ml, 8.0 mmol) was added and the resulting solution was cooled to 0° C. Mesylchloride (200 µl, 2.6 mmol) was added and the solution was stirred for 30 min. The reaction was quenched with a cold, saturated sodium hydrogencarbonate solution (5 ml). The solution was extracted three times with cold chloroform (10 ml). The organic phases were combined and the solvent removed under reduced pressure. The crude product was purified by column chromatography (silica gel, 40 g, elution with methylene chloride/methanol 97:3). Yield: 96 mg (43%).

R$_f$=0.55 (methylene chloride/methanol 9:1).

$^1$H-NMR (500 MHz, CDCl$_3$): δ=1.37 (s, 3H; acetonide-H), 1.45–1.48 (m, 2H; linker-H), 1.59–1.61 (m, 5H; linker-H and acetonide-H), 2.85(s, 6H; N(CH$_3$)$_2$), 2.96 (s, 3H; SO$_2$CH$_3$), 2.98–3.02 (m, 2H; linker-H), 3.32–3.36 (m, 2H; linker-H), 4.33–4.43 (m, 3H; 5'-H and 4'-H), 5.03 (dd, $^3$J=9.8, 6.1 Hz, 1H; 3'-H), 5.52 (dd, $^3$J=2.5, 6.5 Hz, 1H; 2'-H), 6.04 (d, $^3$J=2.5 Hz, 1H; 1'-H), 6.13 (s, br., 2H; 6-NH$_2$), 6.91 (t, $^3$J=5.8 Hz, 1H; 8-NH), 7.13 (d, $^3$J=7.3 Hz, 1H; arom.-H), 7.43 (t, $^3$J=8.2 Hz, 1H; arom.-H), 7.50 (t, $^3$J=7.9 Hz, 1H, arom.-H), 8.10 (s, 1H; 2-H), 8.23 (d, $^3$J=7.0 Hz, 1H; arom.-H), 8.37 (d, $^3$J=8.5 Hz, 1H; arom.-H), 8.51 (d, $^3$J=8.6 Hz, 1H; arom.-H).

$^{13}$C-NMR (125.7 MHz, CDCl$_3$): δ=24.62 (q; acetonide-CH$_3$), 25.30 (t; linker-C), 26.89 (t; linker-C), 27.04 (q; acetonide-CH$_3$), 37.50 (q; SO$_2$CH$_3$), 41.58 (t; linker-C), 42.70 (t; linker-C), 45.44(q; N(CH$_3$)$_2$), 68.38 (t; 5'-C), 80.10 (d; 3'-C), 82.11 (d; 2'-C), 83.29 (d; 4'-C), 88.63 (d; 1'-C), 115.16 (d; arom.-C), 118.94 (d; arom.-C), 123.23 (d; arom.-C), 128.20 (d; arom.-C), 129.70 (d; arom.-C), 130.37 (d; arom.-C), 149.78 (d; 2-C), 151.84 (s), 152.41 (s).

ESI-MS: m/z (%): 705.3 (70) [M+H]$^+$, 609.7 (100) [cyclonucleoside+H]$^+$.

1.4 8-Amino[1"-(N"-dansyl)-4"-aminobutyl]-5'-O-mesyl adenosine, Compound 13.

Nucleoside. 12 (96.2 mg, 0.14 mmol) was dissolved in aqueous formic acid (50%, 10 ml), and the resulting solution was stirred at room temperature for 4 d. After complete conversion the solvent was removed under reduced pressure and remaining solvent was coevaporated with a mixture of water and methanol (1:1, 5 ml). The crude product was purified by column chromatography (silica gel, 15 g, elution with methylene chloride/methanol 9:1). Yield: 49.2 mg (55%).

R$_f$=0.23 (methylene chloride/methanol 9:1).

$^1$H-NMR (500 MHz, DMSO-d$_6$): δ 1.36–1.42 (m, 2H; linker-H), 1.47–1.53 (m, 2H; linker-H), 2.77–2.79 (m, 2H; linker-H), 2.81 (s, 6H; N(CH$_3$)$_2$), 3.07 (s, 3H; SO$_2$CH$_3$), 3.17–3.20 (m, 2H; linker-H), 4.01–4.04 (m, 1H; 4'-H), 4.33–4.47 (m, 3H; 5'-H and 3'-H), 5.08 (ddd=q, $^3$J=5.5 Hz, 1H; 2'-H), 5.37 (d, $^3$J=5.5 Hz, 1H; OH), 5.44(d, $^3$J=5.5 Hz, 1H; OH), 5.72 (d, $^3$J=5.1 Hz, 1H; 1'-H), 6.48 (s, br., 2H; 6-NH$_2$), 6.78 (t, $^3$J=5.3 Hz, 1H; 8-NH), 7.24 (d, $^3$J=7.8 Hz, 1H; arom.-H), 7.57 (t, $^3$J=8.3 Hz, 1H; arom.-H), 7.61 (t, $^3$J=7.8 Hz, 1H; arom.-H), 7.88 (s, 1H; 2-H), 7.95 (t, $^3$J=5.7 Hz, 1H; NHSO$_2$), 8.08 (d, $^3$J=6.9 Hz, 1H; arom.-H), 8.28 (d, $^3$J=8.7 Hz, 1H; arom.-H), 8.44 (d, $^3$J=8.7 Hz, 1H; arom.-H).

$^{13}$C-NMR (125.7 MHz, DMSO-d$_6$): δ=27.24 (t; linker-C), 28.06 (t; linker-C), 37.91 (q; SO$_2$CH$_3$), 43.07 (t; linker-C), 43.58 (t; linker-C), 46.41 (q; N(CH$_3$)$_2$), 71.21 (t; 5'-C), 71.45 (d; 3'-C), 71.61 (d; 2'-C), 82.20 (d; 4'-C), 88.63(d; 1'-C), 116.44 (d; arom.-C), 118.76 (s), 120.46 (d; arom.-C), 124.98 (d; arom.-C), 129.16 (d; arom.-C), 129.54 (d; arom.-C), 130.34 (s), 130.39 (d; arom.-C), 130.68 (s), 137.35 (s), 149.95 (d; 2-C), 150.78 (s), 152.66 (s), 153.06 (s), 153.73 (s).

ESI-MS: m/z (%): 665.6 (85) [M+H]$^+$, 687.4 (100) [M+Na]$^+$.

1.5 Synthesis of 8-Amino[1"-(N"-dansyl)-4"-aminobutyl]-5'-(1-aziridinyl)-5'-deoxy adenosine, Compound 9

Nucleoside 13 (20 mg, 30 pmol) was dissolved in dry aziridine (S. Gabriel, Chem. Ber. 1888, 21, 2664–2669; S. Gabriel, R. Stelzner, Chem. Ber. 1895, 28, 2929–2938) (1 ml) and N-ethyldiisopropylamine (350 µl) under an argon atmosphere, and stirred at room temperature for 3 d. The reaction was monitored by analytical reversed-phase HPLC (Hypersil-ODS, 5 µm, 120 Å, 250×4.6 mm, Bischoff, Leonberg, Germany). Compounds were eluted with acetonitrile (0% for 5 min, followed by a linear gradientto 35% in 30 min and to 70% in 10 min, 1 ml/min) in triethylammonium acetate buffer (0.1 M, pH=7.0). The solvent was removed under reduced pressure after completeness of the reaction. The crude product was purified by column chromatography (silica gel, 2 g, elution with methylene chloride/methanol 9:1). Yield: 6.7 mg (36%).

R$_f$=0.23 (methylene chloride/methanol 9:1).

$^1$H-NMR (500 MHz, DMSO-d$_6$): δ=1.19–1.22 (m, 2H; aziridine-H), 1.32–1.34 (m, 2H; linker-H), 1.37–1.39 (m, 2H; linker-H), 1.59–1.61 (m, 2H; aziridine-H), 1.94 (dd, $^3$J=3.2 Hz, $^2$J=13.5 Hz, 1H; 5H$_a$), 2.74–2.79 (m, 2H; linker-H), 2.81 (s, 6H; N(CH$_3$)$_2$), 2.91–2.95 (m, 1H; 5'-H$_b$), 3.07–3.16 (m, 2H; linker-H), 3.94–3.96 (m, 1H; 4'-H), 4.19–4.21 (m, 1H; 3'-H), 4.634.67 (m, 1H; 2'-H), 5.20(d, $^3$J=4.1 Hz, 1H; OH), 5.30 (d, $^3$J=6.8 Hz, 1 H; OH), 5.90 (d, $^3$J=7.2 Hz, 1H; 1'-H), 6.42 (s, br., 2H; 6-NH$_2$), 7.23 (d, $^3$J=7.2 Hz, 1H; arom.-H), 7.55–7.61 (m, 3H; arom.-H and 8-NH), 7.87 (s, 1H; 2-H), 7.95 (t, $^3$J=5.6 Hz, 1H; NHSO$_2$), 8.08 (d, $^3$J=7.2 Hz, 1H; arom.-H), 8.28 (d, $^3$J=8.6 Hz, 1H; arom.-H), 8.43 (d, $^3$J=8.6 Hz, 1H; arom.-H).

$^{13}$C-NMR (125.7 MHz, DMSO-d$_6$): δ=26.92 (t; aziridine-C), 27.43 (t; linker-C), 28.01 (t; linker-C), 30.02 (t; aziridine-C), 43.02 (t; linker-C), 43.65 (t; linker-C), 46.41 (q; N(CH$_3$)$_2$), 62.96 (t; 5'-C), 71.14 (d; 2'-C), 72.29 (d; 3'-C), 85.31 (d; 4'-C), 87.11 (d; 1'-C), 116.45 (d; arom.-C), 118.20 (s), 120.45 (d; arom.-C), 124.96 (d; arom.-C), 129.16 (d; arom.-C), 129.57 (d; arom.-C), 130.00 (s), 130.36 (d; arom.-C), 130.68 (s), 137.37 (s), 149.86 (d; 2-C), 151.49 (s), 152.42 (s), 152.66 (s), 153.43 (s).

ESI-MS: m/z (%): 612.7 (100) [M+H]$^+$.

2. Enzyme Reaction With the N6-adenine DNA methyltransferase M•TaqI. (Scheme 7)

Figure 5:
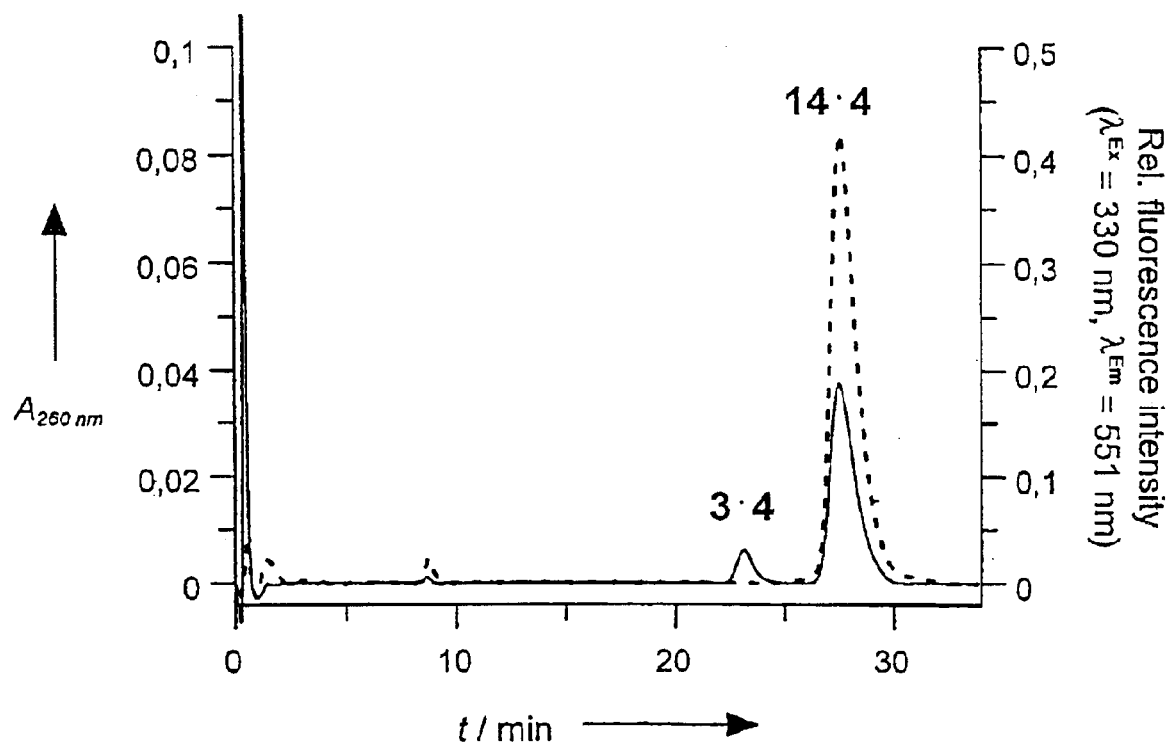
FIG. 5 shows the anion exchange chromatography (UV- and fluorescence detection) of the enzyme reaction with M•TaqI of Example 2.

The enzyme-catalyzed reaction was carried out in a mixture (500 µl) of cofactor free M-Taql (5 nmol, 10 µM), duplex oligodeoxynucleotide 3•4 (5 nmol, 10 µM), compound 9 (10 nmol, 20 µM), Tris acetate (20 mM, pH 6.0), potassium acetate (50 mM), magnesium acetate (10 mM) and Triton X-100 (0,01%) at 37° C. The progress of the reaction was monitored by anion exchange chromatography (Poros 10 HQ, 10 μm, 4,6×10 mm, PerSeptive Biosystems, Germany). Compounds were eluted with aqueous potassium chloride (0.2 M for 5 min, followed by a linear gradient to 0.5 M in 5 min and to 1 M in 30 min) in Tris chloride buffer (10 mM, pH 7.0). Complete conversion to a new product (containing DNA and protein) with a retention time of 7.9 min was observed after 15 h. (No conversion of the duplex oligodeoxynucleotide 3•4 was observed in a parallel control experiment without M•TaqI.) For the fragmentation of the obtained protein-DNA complex the reaction solution was treated with a potassium hydroxide solution (10 M) to adjusted the pH to 8.0. Then, a solution (4 μl) of proteinase K (31 mg/ml), Tris chloride (50 mM, pH 8.0) and calcium chloride (1 mM) was added, and the reaction mixture was incubated at 37° C. for 1 h. The proteolytic fragmentation was monitored by anion exchange chromatography as described above. The fluorescent species with a retention time of 7.9 min disappeared and the new fluorescent compound 144 with a retention time of 29.2 min was formed (FIG. 5). For further characterization the product 144 was isolated by reversed phase chromatography (column: Hypersil-ODS, 5 μm, 120 Å, 250×4.6 mm, Bischoff, Leonberg, Germany; elution: triethylammonium-acetate buffer, 0.1 M, pH 7.0 for 5 min, followed by a linear acetonitrile gradient to 35% in 30 min, 1 ml/min).

Analysis of the product duplex oligodeoxynucleotide 14.4 by enzymatic fragmentation: Purified 144 (0.57 OD at 260 nm) was dissolved in potassium phosphate buffer (10 mM, pH 7.0, 228 μl) containing magnesium chloride (10 mM), DNase I (2.7 U), phosphodiesterase from *Crotalus durissus* (0.041 U), phosphodiesterase from calf spleen (0.055 U) and alkaline phosphatase (13.7 U) and incubated at 37° C. for 20 h. An aliquot (100 μl) was injected onto a reversed-phase HPLC column (Hypersil-ODS, 5 μm, 120 Å. 250×4.6 mm, Bischoff, Leonberg, Germany), and the products were eluted with a gradient of acetonitrile (0–10.5% in 30 min followed by 10.5–28% in 10 min and 28–70% in 15 min, 1 ml/min) in triethylammonium acetate buffer (0.1 M, pH 7.0). Beside the deoxynucleosides dC, dA, dG, T, and $dA^{Me}$ a new fluorescent compound eluting after 49 min was found. This new compound was isolated and detected as positively charged ion at m/z 863.1 by ESI-MS (LCQ connected to a nanoelectrospray ion source, Finnigan MAT, Germany). The observed mass is in good agreement with the calculated molecular mass (863.4) of a protonated, with 9 modified 2'-deoxyadenosine.

3. Fluorescent Labeling 3.1 Fluorescent Labeling of Plasmid DNA Using the N6-adenine DNA methyltransferase M•TaqI.

Figure 6:
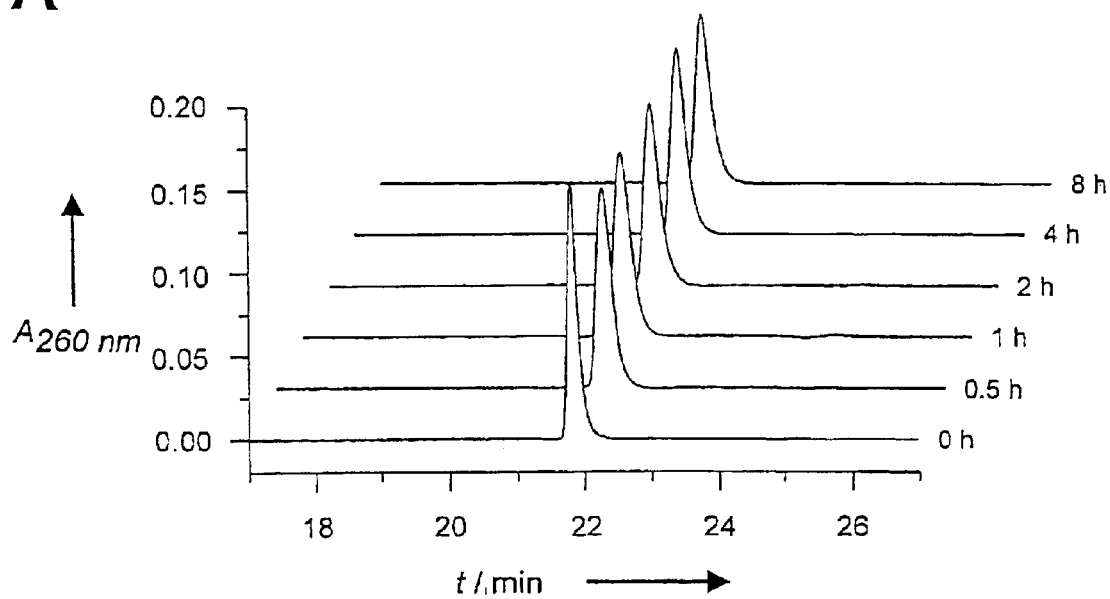
FIG. 6 shows the chromatogram of labeled plasmid DNA (Example 2, labeling 3.1 with M-Taql) of the anion exchange chromatography after different incubation times (6A: UV detection at 260 nm; 6B: fluorescence detection).
Figure 6:
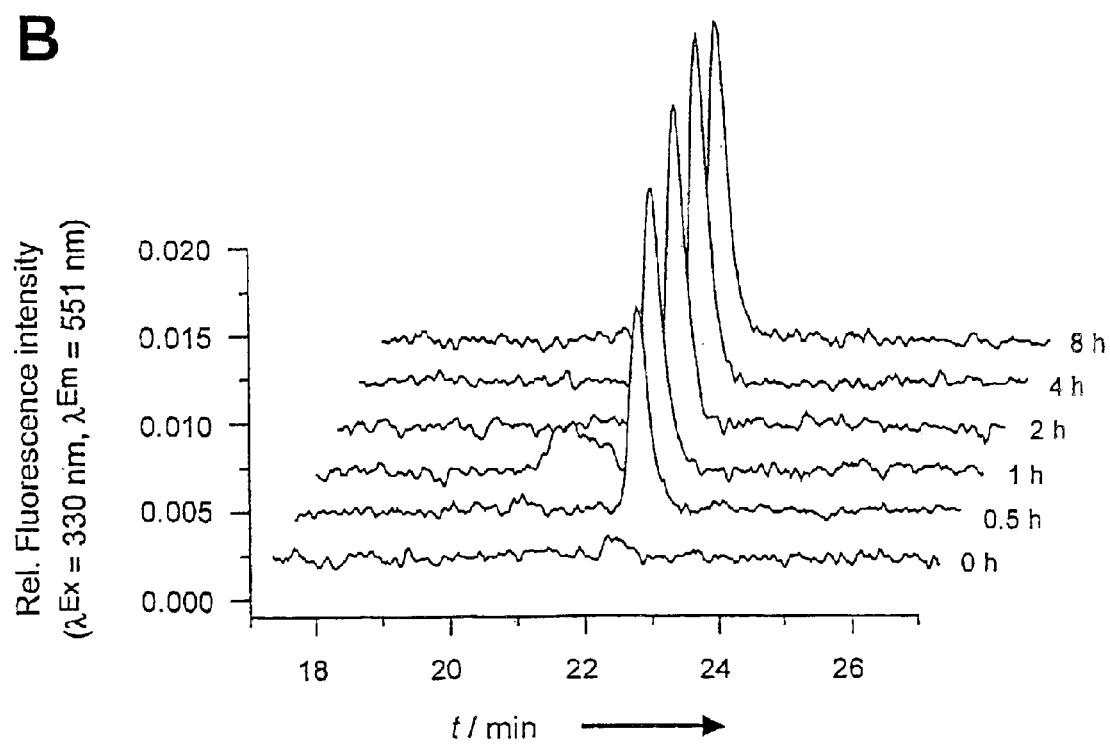
Figure 7:
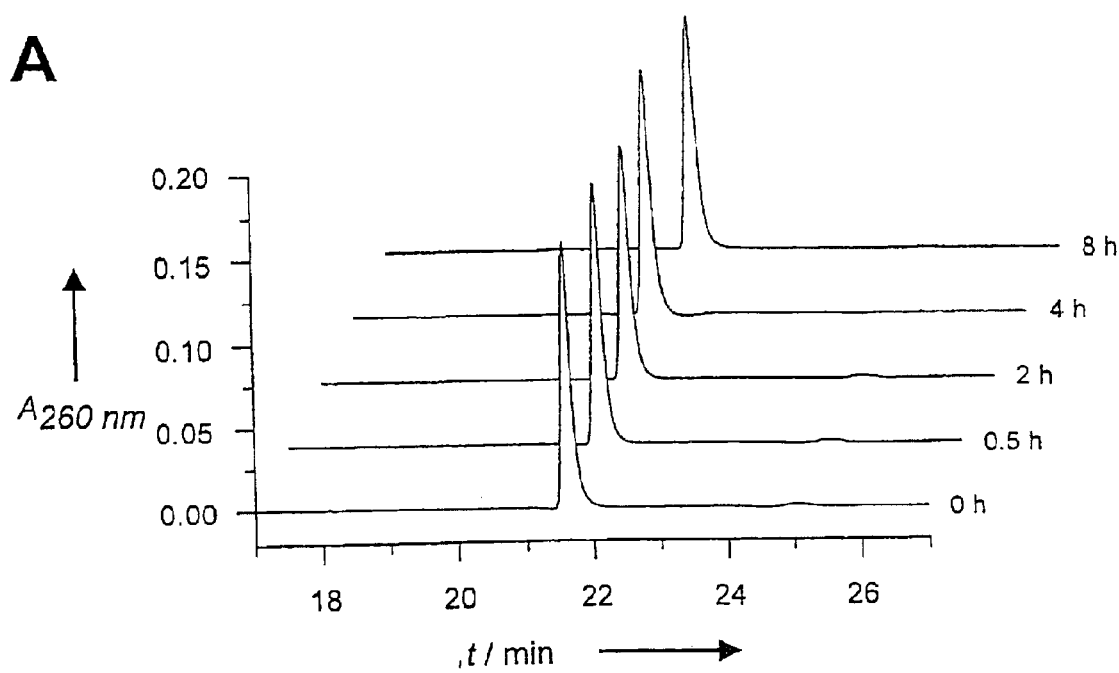
FIG. 7 shows the chromatograms (7A: UV detection at 260 nm; 7B: fluorescence detection) obtained for non-labeled pUC19 (Example 2, labeling 3.1 without M•TaqI) for comparison reasons.
Figure 7:
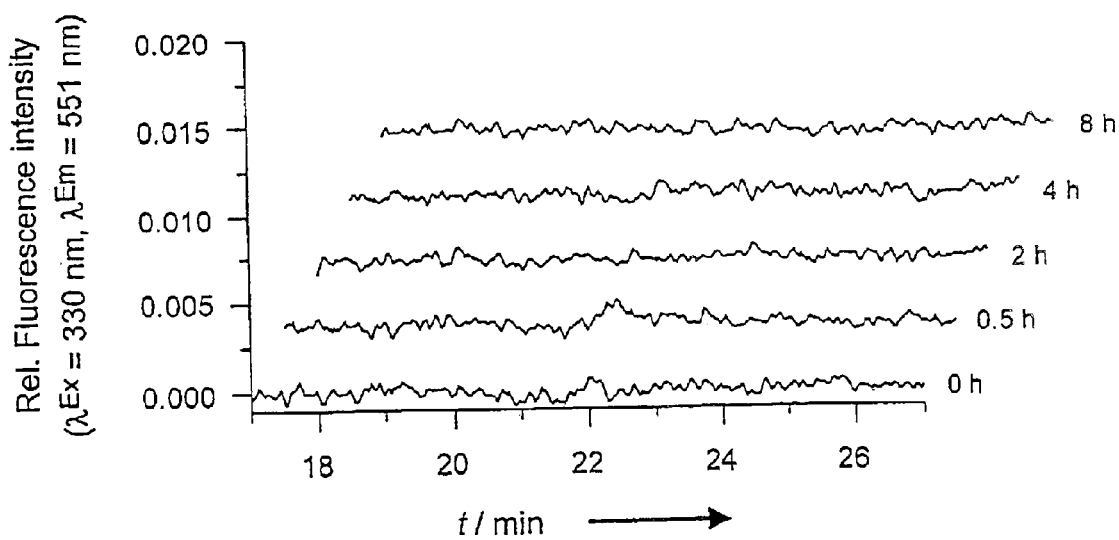

The enzyme-catalyzed labeling reaction was carried out in a mixture (500 μl) of cofactor free M•TaqI (133 nM), pUC19 DNA (28 nM, 4 recognition sites for M•TaqI), compound 9 (20 μM), Tris acetate (20 mM, pH 6,0), potassium acetate (50 mM), magnesium, acetate (10 mM) and Triton X-100 (0,01%) at 65° C. The progress of the reaction was monitored by anion exchange chromatography (NUCLEOGEN DEAE 4000-7, 7 μm, 125×6,2 mm, Machery-Nagel, Düren, Germany). Compounds were eluted with aqueous potassium chloride (0.2 M for 5 min followed by a linear gradient to 1 M in 30 min) in Tris chloride buffer (10 mM, pH 7.0) containing acetonitrile (20%). The chromatograms of the anion exchange chromatography after different incubation times are shown in FIG. 6 (A: UV detection at 260 nm; B: fluorescence detection). The delay between the observed UV absorption and the fluorescence is due to a spatial separation of the UV detector and the fluorescence detector. The labeling reaction yielding fluorescent pUC19 was completed after 8 h. No fluorescently labeled pUC19 was observed in a parallel control experiment without M. Taql (FIGS. 7A and 7B).

3.2 Fluorescent Labeling of Plasmid DNA Using the C5cytosine DNA methyltransferase M•HhaI.

Figure 8:
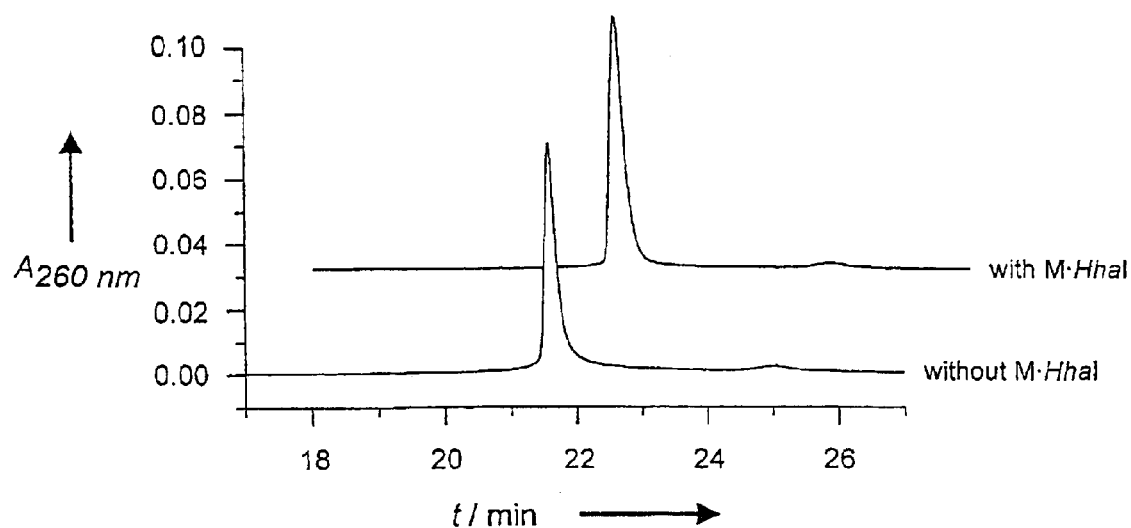
FIG. 8 shows the chromatograms (8A: UV detection at 260 nm; 8B: fluorescence detection) of labeled and non-labeled pUC19 (Example 2, labeling 3.2 with and without M•HhaI)
Figure 8:
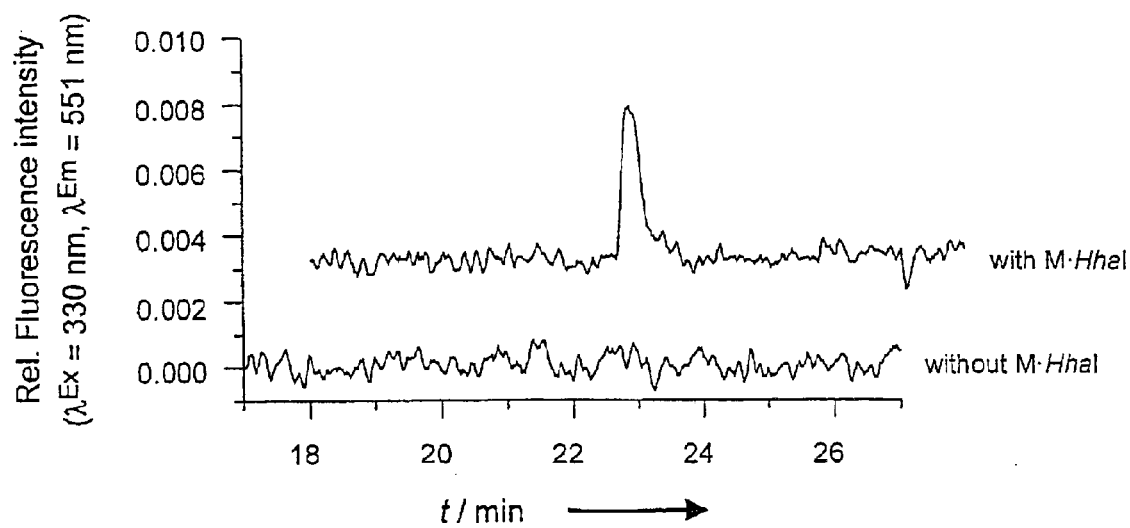

The enzyme-catalyzed labeling reaction was carried out in a mixture (100 μl) of M-HhaI (730 nM), pUC19 DNA (40 nM, 17 recognition sites for M•HhaI), compound 9 (20 μM), Tris chloride (10 mM, pH 6.85), sodium chloride (50 mM), EDTA (0,5 mM) and P-mercaptoethanol (2 mM) at 37° C. A parallel control experiment was performed without M•HhaI. Aliquots of both incubations after 20 h reaction time were analyzed by anion exchange chromatography as described above (see example 2, 3.1). The obtained chromatograms are shown in FIG. 8 (A: UV detection at 260 nm; B: fluorescence detection). No fluorescent labeling was observed in absence of M•HhaI.

---

What is claimed is:

1. A compound of Formula (I):

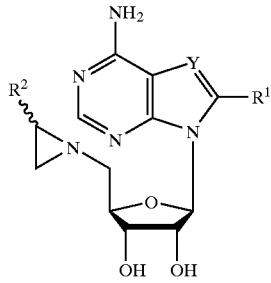

(I)

wherein Y is N or —$CR^3$, $R^1$ and $R^3$ independently from each other are H, $H^3$, —$NH(CH_2)_nNHR^4$ or —$NH(C_2H_5O)_nC_2H_5NHR^4$, with $R^4$ selected from the group consisting of fluorophores, affinity tags, crosslinking agents, chromophors, proteins, peptides, amino acids, nucleotides, nucleosides, nucleic acids, carbohydrates, lipids, PEG, transfection reagents, beads and intercalating agents, and n being an integer from 1 to 250, and $R^2$ is selected from H, $^3H$, and —$CH_2CH(COOH)(NH_2)$, provided when $R^1$ is —$NH(CH_2)_nNHR^4$ or —$NH(C_2H_5O)_nC_2H_5NHR^4$, Y is N or CH; and when $R^3$ is —$NH(CH_2)_nNHR^4$ or —$NH(C_2H_5O)_nC_2H_5NHR^4$, $R^1$ is H.

2. The compound of claim 1 where Y is N.

3. The compound of claim 2 where $R^1$ is —$NH(CH_2)_nNHR^4$ and $R^2$ is hydrogen.

4. The compound of claim 3 wherein n is 1–20.

5. The compound of claim 4 wherein $R^4$ is selected from flourophores, affinity tags, crosslinking agents and chromophors.

6. The compound of claim 5 wherein the fluorophore is BODIPY, coumarin, dansyl, florescein, mansyl, pyrene, rhodamines, Texas red, TNS, the cyanine fluorophores Cy2, Cy3, Cy3.5, Cy5, Cy5.5, and Cy7.

7. The compound of claim 6 wherein the fluorophore is dansyl.

8. The compound of claim 7 wherein n is 4.

9. The compound of claim 2 wherein $R^1$ and $R^2$ are each hydrogen.

10. The compound of claim 2 wherein $R^1$ is hydrogen and $R^2$ is —$CH_2CH(COOH)(NH_2)$.

11. The compound of claim 1 wherein Y is $CR^3$ and $R^1$ is hydrogen.

12. The compound of claim 11 where $R^3$ and $R^2$ are each hydrogen.

13. The compound of claim 11 wherein $R^3$ is hydrogen and $R^2$ is —$CH_2CH(COOH)(NH_2)$.

14. The compound of claim 11 wherein $R^3$ is —$NH(CH_2)_nNHR^4$ and $R^2$ is hydrogen.

15. The compound of claim 14 wherein n is 1–20.

16. The compound of claim 15 wherein $R^4$ is selected from flourophores, affinity tags, crosslinking agents and chromophors.

17. The compound of claim 16 wherein the fluorophore is BODIPY, coumarin, dansyl, florescein, mansyl, pyrene, rhodamines, Texas red, TNS, the cyanine fluorophores Cy2, Cy3, Cy3.5, Cy5, Cy5.5, and Cy7.

18. The compound of claim 17 wherein the fluorophore is dansyl.

19. The compound of claim 18 wherein n is 4.

20. The compound of claim 5 or claim 16 wherein the affinity tag is a peptide tag, biotin, digoxigenin or dinitrophenol.

21. The compound of claim 20 wherein the peptide tag is his-tag, or a tag having metal chelating capability that can be used in IMAC, strep-tag, flag-tag, c-myc-tag, epitopes or gultathinone.

22. The compound of claim 5 or claim 16 wherein the crosslinking agent is maleimide, iodoacetamide or a photo crosslinking agent.

23. The compound of claim 22 wherein the photo crosslinking agent is arylazide, a diazo compound or a benzophenone compound.

24. A compound of Formula (II):

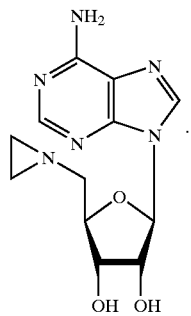

(II)

25. A compound of Formula (III):

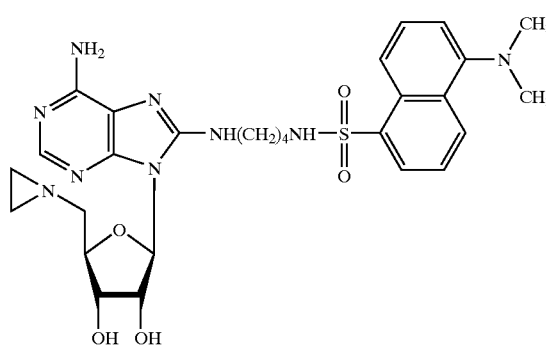

(III)

26. A complex comprising a compound of claim 1 and a methyltransferase capable of using S-adenosyl-L-methionine (SAM) as a cofactor.

27. The complex of claim 26 wherein the methyl transferase targets a target molecule selected from the group consisting of a nucleic acid, a polypeptide, a protein, an enzyme and a small molecule.

28. The complex of claim 27 wherein the nucleic acid is a DNA or an RNA.

29. The complex of claim 28 wherein the DNA is M.Taql or M.Hhal.

30. The complex of claim 29 comprising a compound of Formula (II):

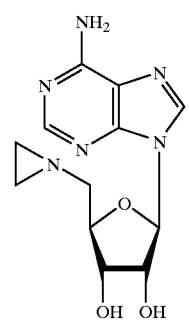

(II)

and M.Taql.

31. The complex of claim 29 comprising a compound of Formula (II):

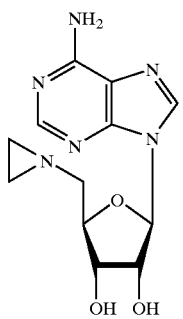

(II)

and M.Hhal.

32. The complex of claim 29 comprising a compound of Formula (III):

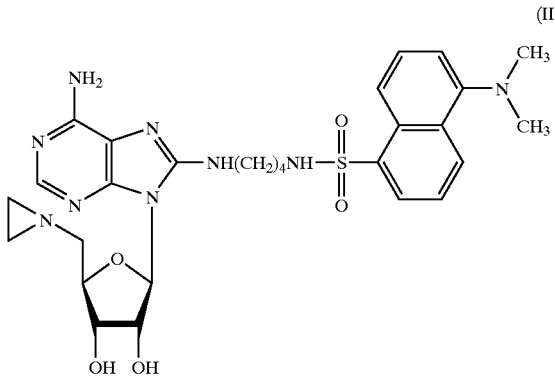

(III)

and M.Taql.

33. The complex of claim 26 wherein the methyltransferase is part of a restriction modification system of a bacterium.

34. The complex of claim 26, wherein the methyltransferase methylates proteins at distinct amino acids.

35. A kit comprising a compound of claim 1.

36. A kit comprising a complex of claim 26.

37. A pharmaceutical composition comprising a compound of claim 1.

38. A pharmaceutical composition comprising a complex of claim 26.

39. A diagnostic composition comprising a compound of claim 1.

40. A diagnostic composition comprising a complex of claim 26.

41. A method for modifying a target molecule comprising the following steps:
   providing a compound of claim 1;
   providing a methyltransferase capable of using S-adenosyl-L-methionine (SAM) as a co-factor;
   providing a target molecule, the target molecule being a suitable substrate of the methyltransferase; and
   contacting the target molecule with the compound in the presence of the methyltransferase such that the target molecule is modified by the compound.

42. The method of claim 41, wherein the modification of the target molecule is achieved by using the compound as a cofactor of the methyltransferase which transfers the compound or part of the compound onto the target molecule.

43. The method of claim 41, wherein the target molecule is a nucleic acid molecule, a polypeptide, a synthetic polymer or a small molecule.

44. The method of claim 43, wherein the nucleic acid molecule is DNA, RNA or a hybrid thereof.

45. The method of claim 43, wherein the small molecule is a lipid.

46. The method of claim 43, wherein the polypeptide is a protein or a fusion protein comprising a methylation site.

47. A method for preparing a modified target molecule comprising the following steps:

provided a compound of claim 1;

providing a methyltransferase capable of using S-adenosyl-L-methionine (SAM) as a co-factor;

providing a target molecule, the target molecule being a suitable substrate of the methyltransferase; and incubating the target molecule with the compound in the presence of the methyltransferase under conditions which allow the transfer of the compound or part of it onto the target molecule.

48. The method of claim 47, wherein the target molecule comprises a nucleic acid molecule, a DNA, an RNA, an RNA/DNA hybrid, a polypeptide, a fusion protein, a synthetic polymer, a small molecule or a lipid.

49. A compound prepared by the method of claim 47.

* * * * *

SEQUENCE LISTING

```
<160> NUMBER OF SEQ ID NOS: 4

<210> SEQ ID NO 1
<211> LENGTH: 14
<212> TYPE: DNA
<213> ORGANISM: Artificial Sequence
<220> FEATURE:
<223> OTHER INFORMATION: synthetically generated oligonucleotide

<400> SEQUENCE: 1
gccgctcgat gccg                                                      14

<210> SEQ ID NO 2
<211> LENGTH: 14
<212> TYPE: DNA
<213> ORGANISM: Artificial Sequence
<220> FEATURE:
<223> OTHER INFORMATION: synthetically generated oligonucleotide
<221> NAME/KEY: modified_base
<222> LOCATION: 9
<223> OTHER INFORMATION: methylated adenosine
```

```
<400> SEQUENCE: 2
cggcatcgag cggc                                                           14

<210> SEQ ID NO 3
<211> LENGTH: 12
<212> TYPE: DNA
<213> ORGANISM: Artificial Sequence
<220> FEATURE:
<223> OTHER INFORMATION: synthetically generated oligonucleotide

<400> SEQUENCE: 3
tgtcaggcat ga                                                             12

<210> SEQ ID NO 4
<211> LENGTH: 13
<212> TYPE: DNA
<213> ORGANISM: Artificial Sequence
<220> FEATURE:
<223> OTHER INFORMATION: synthetically generated oligonucleotide
<221> NAME/KEY: modified_base
<222> LOCATION: 6
<223> OTHER INFORMATION: methylated cytosine

<400> SEQUENCE: 4
tcatgcgctg aca                                                            13
```